United States Patent
Mao

(10) Patent No.: US 12,203,948 B2
(45) Date of Patent: Jan. 21, 2025

(54) COMPOSITIONS AND METHODS FOR THE DETECTION OF HOST CELL PROTEINS

(71) Applicant: LONZA LTD., Visp (CH)

(72) Inventor: Guojie Mao, Slough (GB)

(73) Assignee: LONZA LTD, Visp (CH)

( * ) Notice: Subject to any disclaimer, the term of this patent is extended or adjusted under 35 U.S.C. 154(b) by 62 days.

(21) Appl. No.: 17/735,524

(22) Filed: May 3, 2022

(65) Prior Publication Data

US 2022/0268791 A1    Aug. 25, 2022

Related U.S. Application Data

(63) Continuation of application No. 16/093,253, filed as application No. PCT/EP2017/058775 on Apr. 12, 2017, now Pat. No. 11,353,468.

(60) Provisional application No. 62/322,621, filed on Apr. 14, 2016.

(51) Int. Cl.
| | |
|---|---|
| *G01N 33/53* | (2006.01) |
| *C07K 16/00* | (2006.01) |
| *C07K 16/06* | (2006.01) |
| *C07K 16/18* | (2006.01) |
| *G01N 33/543* | (2006.01) |
| *G01N 33/94* | (2006.01) |

(52) U.S. Cl.
CPC ............. *G01N 33/94* (2013.01); *C07K 16/00* (2013.01); *C07K 16/065* (2013.01); *C07K 16/18* (2013.01); *G01N 33/543* (2013.01); *C07K 2317/14* (2013.01)

(58) Field of Classification Search
None
See application file for complete search history.

(56) References Cited

U.S. PATENT DOCUMENTS

| 6,797,522 B1 | 9/2004 | Still et al. |
| 8,728,828 B2 | 5/2014 | Berg et al. |
| 11,353,468 B2 * | 6/2022 | Mao .......................... A61P 7/04 |
| 2006/0205010 A1 | 9/2006 | Allioux et al. |
| 2008/0261249 A1 | 10/2008 | Wang et al. |
| 2014/0255423 A1 | 9/2014 | Hickman et al. |

FOREIGN PATENT DOCUMENTS

| WO | 1999/034220 A2 | 7/1999 |
| WO | 2005/071410 A1 | 8/2005 |
| WO | 2015/038888 A1 | 3/2015 |
| WO | 2017/178526 A1 | 10/2017 |

OTHER PUBLICATIONS

Chimento et al., Developing Antibodies for Detection of Host Cell Protein Contaminants, Genetic Engineering and Biotechnology News, Jan. 27, 2014, pp. 1-7 (Year: 2014).*
Bengt Guss, et al., "Structure of The IgG-BINDING Regions of Streptococcal Protein G", The EMBO Journal, vol. 5, No. 7, pp. 1567-1575, 1986.
Fan et al. "The use of glutamine synthetase as a selection marker: recent advances in Chinese hamster ovary cell line generation processes" Pharm. Bioprocess. (2013) vol. 1, No. 5, pp. 487-502 2008.
GE Healthcare, Protein Sample Preparation, Instructions 28-9067-73 AC, 8 pages, 2008.
Hogwood et al. "Measurement and control of host cell proteins (HCPs) in CHO cell bioprocesses" Current Opinion in Biotechnology (2014) vol. 30, pp. 153-160.
International Search Report and Written Opinion for corresponding International Application No. PCT/EP2017/058775 dated Sep. 5, 2017 (18 pages).
Krawitz et al., "Proteomic studies support the use of multi-product immunoassays to monitor host cell protein impurities" Proteomics. Jan. 2006;6(1):94-110.
Lonza "GS Gene expression system" GS Bibliography (2016) Revision 32, pp. 1-47.
Margareta Eliasson, et al., "Chimeric IgG-BINDING Receptors Engineered From Staphylococcal Protein A and Streptococcal Protein G", The Journal of Biological Chemistry, vol. 23, No. 25, pp. 4323-4327, 1988.
PCT Invitation to Pay Additional Fees and/or Protest Fees for International Application No. PCT/EP2017!058775 dated Jun. 19, 2017 (15 pages).
Tscheliessnig et al. "Host cell protein analysis in therapeutic protein bioprocessing—methods and applications." Biotechnology journal vol. 8, 6 (2013): 655-70.
Wan et al., "An enzyme-linked immunosorbent assay for host cell protein contaminants in recombinant PEGylated staphylokinase mutant SY161", Journal of Pharmaceutical and Biomedical Analysis, vol. 28, 2002, pp. 953-963. (Year: 2002).
Jing Wang; et al., "Preparation, affinity purification and identification of polyclonal antibody against CMTM1-v17/CKLFSF1-v17", Chinese Journal of Immunology, Vo. 22, No. 12, Dec. 20, 2006, pp. 1132-1136 (See English Abstract and translation of the Second Chinese Office Action.).
Min Song; et al., "Preparation and Identification of anti-CD26 Polyclonal antibody", Chinese Journal of Blood Transfusion, vol. 22, No. 7, Jul. 25, 2009, pp. 535-538 (See English Abstract and translation of the Second Chinese Office Action.).
Na Zhang; et al., "Preparation and application of polyclonal antibody against chicken-derived high mobility group protein B1", Chinese Journal of Cellular and Molecular Immunology, vol. 30, No. 3, pp. 284-288 (See English Abstract and translation of the Second Chinese Office Action.), 2014. English portions only.

(Continued)

*Primary Examiner* — Gary Counts
(74) *Attorney, Agent, or Firm* — Dority & Manning, P.A.

(57) ABSTRACT

A method for producing a purified polyclonal anti-HCP antibody preparation is disclosed. The method can comprise acquiring a sample comprising antibodies from an animal immunized with HCP of a host cell, separating antibodies from the sample by contacting the sample with a protein A affinity reagent to provide an antibody preparation, separating anti-HCP antibody from the antibody preparation by contacting the antibody preparation with an HCP-affinity reagent comprising HCP coupled to a substrate, and isolating the separated polyclonal anti-HCP antibody preparation.

8 Claims, 1 Drawing Sheet

(56) References Cited

OTHER PUBLICATIONS

National Intellectual Property Administration of the People's Republic of China, "Second Office Action" issued in connection with Chinese patent application No. CN201780034661.8, which was dated Mar. 3, 2022, and its full English translation (21 pages).

* cited by examiner

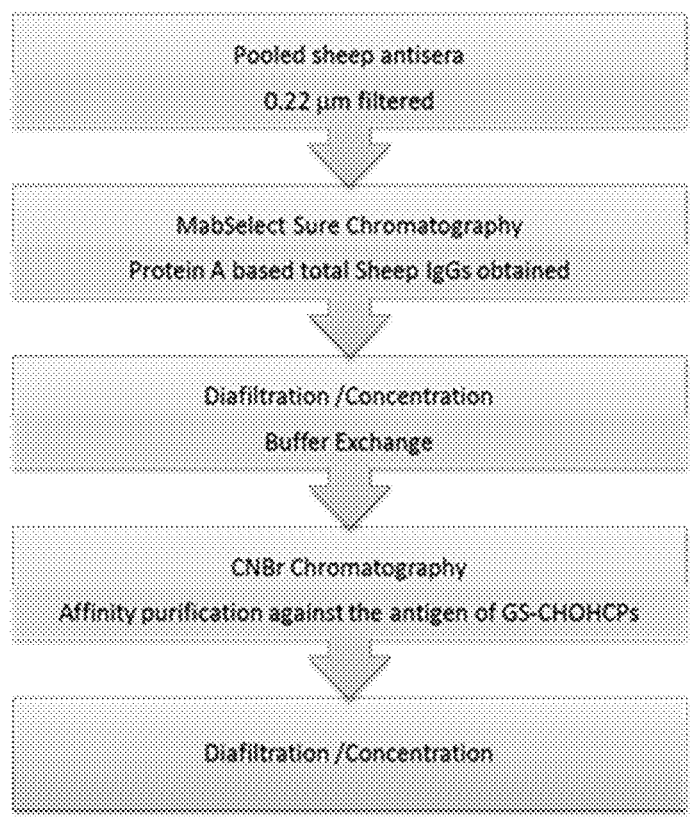

COMPOSITIONS AND METHODS FOR THE DETECTION OF HOST CELL PROTEINS

CROSS-REFERENCES TO RELATED APPLICATIONS

This application is a Continuation of U.S. patent application Ser. No. 16/093,253, which was filed Oct. 12, 2018, now U.S. Pat. No. 11,353,468 issued Jun. 7, 2022, which is a U.S. National Phase Application under 35 U.S.C. § 371 of International Application No. PCT/EP2017/058775, filed Apr. 12, 2017, which in turn claims priority to U.S. provisional application 62/322,621, filed Apr. 14, 2016, the contents of each of which are incorporated herein by reference in their entirety.

FIELD OF THE INVENTION

The present disclosure relates to methods of detecting and/or quantifying host cell protein impurities during the production of a product, e.g., a recombinant protein, e.g., an antibody.

BACKGROUND

Host cell protein (HCP) is an unwanted complex mixture of host proteins which may present in the final product after various manufacturing process. Those HCPs can pose risks to, inter alia, product efficacy and patient safety. Therefore, there is a need for methods for detecting and quantifying HCPs in final biopharmaceutical products.

SUMMARY

The present disclosure provides, inter alia, for a highly sensitive method for the detection of HCPs. In one aspect, disclosed herein are methods of detecting, monitoring, identifying, or quantifying a GS-CHO host cell protein (HCP) in a sample comprising a recombinant polypeptide, the method comprising: a) providing or obtaining a sample comprising a recombinant polypeptide; b) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; d) contacting the immobilized antibody-GS-CHO HCP complex with a detectable antibody that binds to GS-CHO HCPs; e) detecting the presence of GS-CHO HCP bound to the antibody using a detection means for the detectable antibody; and f) optionally quantifying the level of GS-CHO HCP detected; g) optionally identifying one of more of the GS-CHO HCP detected; and h) optionally quantifying one or more of the GS-CHO HCP identified.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, the present disclosure provides methods of manufacturing a recombinant polypeptide drug product, the method comprising: a) providing or obtaining a sample of a recombinant polypeptide preparation; b) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; d) contacting the immobilized antibody-GS-CHO HCP complex with a detectable antibody that binds to GS-CHO HCP; e) quantifying the level of GS-CHO HCP bound to the capture reagent using a detection means for the detectable antibody; and f) processing at least a portion of the preparation as drug product if the level of GS-CHO HCP is below a preselected reference level, thereby manufacturing a recombinant polypeptide drug product.

In some embodiments, the processing comprises one or more of: formulating the polypeptide preparation; processing the polypeptide preparation into a drug product; combining the polypeptide preparation with a second component, e.g., an excipient or buffer; changing the concentration of the polypeptide in the preparation; lyophilizing the polypeptide preparation; combining a first and second aliquot of the polypeptide to provide a third, larger, aliquot; dividing the polypeptide preparation into smaller aliquots; disposing the polypeptide preparation into a container, e.g., a gas or liquid tight container; packaging the polypeptide preparation; associating a container comprising the polypeptide preparation with a label (e.g., labeling); shipping or moving the polypeptide preparation to a different location.

In some embodiments, the processing step comprises combining the polypeptide preparation with an excipient or buffer. In some embodiments, the reference level is about 100 ppm (e.g., less than 100, 90, 80, 70, 60, 50, 40, 30, 20, 10, 5, 1 ppm). In some embodiments, the reference level is between 1 ppm and 1000 ppm. In some embodiments, the reference level is at least 1 ppm, 10 pppm, 50 ppm, 100 ppm, 500 ppm, or 1000 ppm. In some embodiments, the reference level is no greater than 1 ppm, 5 ppm, 10 pppm, 20 ppm, 30 ppm, 40 ppm, 50 ppm, 100 ppm, 500 ppm, or 1000 ppm. In some embodiments, the level of GS-CHO HCP below the reference level is a specification for commercial release of the drug product. In some embodiments, in the level of GS-CHO HCP below the reference level is a specification for commercial release of a drug product under Section 351(a) of the Public Health Service (PHS) Act. In some embodiments, the level of GS-CHO HSP is acquired for one, two, or more samples or batches.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, the present disclosure provides methods of manufacturing a recombinant polypeptide drug product, the method comprising: a) culturing a GS-CHO cell cultured under conditions suitable for production, e.g., expression and secretion, of a recombinant polypeptide, b) separating the secreted recombinant polypeptide from the host cell; c) subjected the secreted recombinant polypeptide to one or more purification steps to produce a recombinant polypeptide preparation; d) taking a sample of a recombinant polypeptide preparation; e) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; f) contacting the immobilized antibody-GS-CHO HCP complex with a detectable antibody that binds to GS-CHO HCP; g) quantifying the level of GS-CHO HCP bound to the capture reagent using a detection means for the detectable antibody; and h) processing at least a portion of the preparation as drug product if the level of GS-CHO HCP is below a preselected reference level, thereby manufacturing a recombinant polypeptide drug product.

In some embodiments, the processing comprises one or more of: formulating the polypeptide preparation; processing the polypeptide preparation into a drug product; combining the polypeptide preparation with a second component, e.g., an excipient or buffer; changing the concentration of the polypeptide in the preparation; lyophilizing the polypeptide preparation; combining a first and second aliquot of the polypeptide to provide a third, larger, aliquot; dividing the polypeptide preparation into smaller aliquots; disposing the polypeptide preparation into a container, e.g., a gas or liquid tight container; packaging the polypeptide preparation; associating a container comprising the polypeptide preparation with a label (e.g., labeling); shipping or moving the polypeptide preparation to a different location.

In some embodiments, the processing step comprises combining the polypeptide preparation with an excipient or buffer. In some embodiments, the reference level is about 100 ppm (e.g., less than 100, 90, 80, 70, 60, 50, 40, 30, 20, 10, 5, 1 ppm). In some embodiments, the reference level is between 1 ppm and 1000 ppm. In some embodiments, the reference level is at least 1 ppm, 10 pppm, 50 ppm, 100 ppm, 500 ppm, or 1000 ppm. In some embodiments, the reference level is no greater than 1 ppm, 5 ppm, 10 pppm, 20 ppm, 30 ppm, 40 ppm, 50 ppm, 100 ppm, 500 ppm, or 1000 ppm. In some embodiments, the level of GS-CHO HCP below the reference level is a specification for commercial release of the drug product. In some embodiments, in the level of GS-CHO HCP below the reference level is a specification for commercial release of a drug product under Section 351(a) of the Public Health Service (PHS) Act. In some embodiments, the level of GS-CHO HSP is acquired for one, two, or more samples or batches.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, the present disclosure provides methods of manufacturing a recombinant polypeptide drug product, the method comprising: a) providing or obtaining a sample of a recombinant polypeptide preparation from culture of a GS-CHO cell; b) acquiring a value for the GS-CHO host cell protein (HCP) in the sample, wherein the value is a function of, is proportional to, or was obtained by, the binding of a polyclonal GS-CHO antibody to the sample, thereby manufacturing a recombinant polypeptide drug product. In some embodiments, the method comprises: evaluating the acquired value, e.g., by comparing the acquired value with a reference value. In some embodiments, the method comprises: responsive to the evaluation, classifying, selecting, accepting, releasing, processing into a drug product, shipping, moving to a different location, formulating, labeling, packaging, releasing into commerce, selling or offering for sale the preparation. In some embodiments, the value was determined by a method described herein.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, the present disclosure provides methods of evaluating a process of manufacturing a recombinant polypeptide in a GS-CHO host cell, the method comprising: a) culturing a GS-CHO cell cultured under conditions suitable for production, e.g., expression and secretion, of a recombinant polypeptide, b) separating the secreted recombinant polypeptide from the host cell to provide a first polypeptide preparation; c) optionally taking a sample of the first polypeptide preparation; d) subjecting the first polypeptide preparation to a purification step to produce a second polypeptide preparation; e) taking a sample of the second polypeptide preparation; f) optionally subjecting the second polypeptide preparation to a second, third, fourth, fifth, or sixth purification step to provide subsequent polypeptide preparations; g) optionally taking a sample of any subsequent polypeptide preparations provided in step f); h) contacting and incubating each of the samples taken with a polyclonal anti-GS-CHO HCP antibody immobilized to a solid support to form an immobilized antibody-GS-CHO HCP complex; i) separating each of the samples from the immobilized antibody-GS-CHO HCP complex; j) contacting the immobilized antibody-GS-CHO HCP complex with a detectable antibody that binds to GS-CHO HCP; k) quantifying the level of GS-CHO HCP bound to the capture reagent using a detection means for the detectable antibody; and l) based on said quantification, making a determination about the process, thereby evaluating a process of manufacturing a recombinant polypeptide.

In some embodiments, the method comprises comparing the level of GS-CHO HCP to a reference level, e.g., wherein if the level of GS-CHO HCP is below the reference level validating the process for use in the production of the recombinant polypeptide.

In some embodiments, the reference level is: i) between 1 ppm and 1000 ppm, ii) at least 1 ppm, 10 pppm, 50 ppm, 100 ppm, 500 ppm, or 1000 ppm, or iii) no greater than 1 ppm, 5 ppm, 10 pppm, 20 ppm, 30 ppm, 40 ppm, 50 ppm, 100 ppm, 500 ppm, or 1000 ppm.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, the present disclosure provides methods of evaluating a process of purifying a recombinant polypeptide, the method comprising: a) subjecting the first polypeptide preparation to a purification step to produce a second polypeptide preparation; b) taking a sample of the second polypeptide preparation; c) optionally subjecting the second polypeptide preparation to a second, third, fourth, fifth, or sixth purification step to provide subsequent polypeptide preparations; d) optionally taking a sample of any subsequent polypeptide preparations provided in step c); e) contacting and incubating each of the samples taken with a polyclonal anti-GS-CHO HCP antibody immobilized to a solid support to form an immobilized antibody-GS-CHO HCP complex; f) separating each of the samples from the immobilized antibody-GS-CHO HCP complex; g) contacting the immobilized antibody-GS-CHO HCP complex with a detectable antibody that binds to GS-CHO HCP; h) quantifying the level of GS-CHO HCP bound to the capture reagent using a detection means for the detectable antibody; and i) based on said quantification, making a determination about the process, thereby evaluating a process of purifying a recombinant therapeutic.

In some embodiments, the method comprises: comparing the level of GS-CHO HCP to a reference level. In some embodiments, the if the level of GS-CHO HCP is below the reference level validating the process for use in the production of the recombinant polypeptide. In some embodiments, the reference level is between 1 ppm and 1000 ppm. In some embodiments, the reference level is at least 1 ppm, 10 pppm, 50 ppm, 100 ppm, 500 ppm, or 1000 ppm. In some embodiments, the reference level is no greater than 1 ppm, 5 ppm, 10 pppm, 20 ppm, 30 ppm, 40 ppm, 50 ppm, 100 ppm, 500 ppm, or 1000 ppm.

In some embodiments, the purification step comprises one or more or any combination of size exclusion chromatography (SEC), ion exchange chromatography (IEX), hydrophobic interaction chromatography (HIC), reverse phase chromatography (RPC), immobilized metal chelate chromatography, ammonium sulfate precipitation, thiophilic adsorption, protein A chromatography, protein G chromatography, protein L chromatography, and affinity chromatography.

In some embodiments, the purification step comprises one or more affinity chromatography steps. In some embodiments, the purification step comprises Protein A chromatography and one or more affinity chromatography steps. In some embodiments, the purification step comprises: protein A chromatography and CNBr chromatography. In some embodiments, the purification step comprises: protein A chromatography and subsequent CNBr chromatography. In some embodiments, the purification step comprises: protein A chromatography and NHS chromatography. In some embodiments, the purification step comprises: protein A chromatography and subsequent NHS chromatography.

In some embodiments, the purification step comprises: i) Protein A chromatography and one or more affinity chromatography steps, ii) protein A chromatography and CNBr chromatography, e.g., protein A chromatography and subsequent CNBr chromatography, or iii) protein A chromatography and NHS chromatography, e.g., protein A chromatography and subsequent NHS chromatography.

In some embodiments, recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin. In some embodiments, the recombinant polypeptide is a therapeutic polypeptide. In some embodiments, the recombinant polypeptide is one disclosed in Table 1. In some embodiments, the recombinant polypeptide is one disclosed in Table 2. In some embodiments, the recombinant polypeptide is an antibody. In some embodiments, the antibody is a monoclonal antibody. In some embodiments, the monoclonal antibody is a therapeutic antibody.

In some embodiments, the sample is derived from a downstream processing step in a production process of the recombinant polypeptide. In some embodiments, the sample is derived from an upstream processing step in a production process of the recombinant polypeptide. In some embodiments, the sample is derived from a final product of the recombinant polypeptide. In some embodiments the method comprises, two, three, four, five, six, seven, eight, nine, ten, or more than ten samples derived from one or more steps in a production process of the recombinant polypeptide. In some embodiments, the detectable antibody is directly detectable. In some embodiments, the detectable antibody is amplified by a fluorimetric reagent. In some embodiments, the detectable antibody is biotinylated and the detection means is avidin or streptavidin-peroxidase and 3,3',5,5'-tetramethyl benzidine.

In one aspect, provided herein are kits comprising: a) a polyclonal anti-GS-CHO HCP antibody immobilized to a solid support; b) optionally a detectable antibody; c) optionally a wash buffer; and d) optionally a detecting reagent. In some embodiments, the detecting reagent is the same as the capture reagent. In some embodiments, the detecting reagent is the same as the capture reagent only modified to be amplified by a fluorimetric reagent. In some embodiments, the detecting antibody is biotinylated and the detection means is avidin or streptavidin-peroxidase and 3,3',5,5'-tetramethyl benzidine.

In one aspect, provided herein are purified preparations of polyclonal anti-GS-CHO antibody. In some embodiments, the the anti-GS-CHO antibody is a sheep antibody. In some embodiments, the anti-GS-CHO antibody is a goat, horse, rabbit, bovine, murine, hamster, or human antibody. In some embodiments, the preparation is substantially free from non-HCP specific IgGs. In some embodiments, the preparation contains no more than 0.5%, 1%, 2%, 3%, 5%, 10%, 20%, 30%, 40%, or 50% non-HCP specific IgGs. In some embodiments, the preparation contains less than 50%, 40%, 30%, 20%, 10%, 5%, 4%, 3%, 2%, 1%, 0.5% non-HCP specific IgGs. In some embodiments, the purified by a method comprising: protein A chromatography, and one or more affinity chromatography steps (e.g., CNBr chromatography, NHS chromatography).

In one aspect, provided herein are reaction mixtures comprising a polyclonal preparation (e.g., a polyclonal preparation described herein) of anti-GS-CHO antibody and a recombinant polypeptide selected from Table 1 or Table 2. In some embodiments, the reaction mixture comprises an antibody that binds to the anti-GS-CHO antibody.

In one aspect, provided herein are methods of determining whether a batch or lot of a recombinant polypeptide drug product meets or satisfies a release specification, wherein the release specification is a preselected reference level of GS-CHO HCP the method comprising: a) providing or obtaining a sample of a recombinant polypeptide preparation; b) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; d) contacting the immobilized antibody-GS-CHO HCP complex with a detectable antibody that binds to GS-CHO HCP; e) quantifying the level of GS-CHO HCP bound to the capture reagent using a detection means for the detectable antibody; and f) processing at least a portion of the preparation as drug product if the level of GS-CHO HCP meets, satisfies, or is below the release specification, thereby determining whether a batch or lot of a recombinant polypeptide drug product meets or satisfies a release specification. In some embodiments, processing comprises: classifying, selecting, accepting, releasing, processing into a drug product, shipping, moving to a different location, formulating, labeling, packaging, releasing into commerce, selling or offering for sale the preparation. In some embodiments, the value was determined by a method described herein.

In one aspect, disclosed herein are methods of making a polyclonal anti-HCP antibody preparation, the method comprising: a) acquiring a sample comprising antibodies, e.g., antisera, from an animal (e.g., a sheep, rabbit, mouse, rat, hamster, goat, etc.) immunized with HCP of a host cell (e.g., a cell line, e.g., a mammalian, rodent, or insect cell or cell line, e.g., a CHO, SP2, NSO host cell); and b) separating anti-HCP antibody from the sample, e.g., by contacting the sample with an HCP-affinity reagent, thereby producing a polyclonal anti-HCP antibody preparation.

In some embodiments, step b) comprises: b.1) separating antibodies, e.g., IgG antibodies, from the sample to provide an antibody preparation; and b.2) separating anti-HCP antibody from the antibody preparation. In some embodiments, separating antibodies comprises contacting the antibodies with an affinity reagent, e.g., protein A. In some embodiments, separating antibodies comprises purifying a polyclonal anti-HCP antibody from the antisera through a purification method comprising protein A chromatography. In some embodiments, separating anti-HCP antibody from the antibody preparation comprises contacting the antibody preparation with an HCP-affinity reagent. In some embodiments, the HCP-affinity reagent comprises HCP coupled to a substrate, e.g., an insoluble or solid substrate, e.g., an agarose bead, e.g., Sepharase, e.g., cyanogen bromide (CNBr) or N-hydroxysuccinimide (NHS) chromatography) derivatized substrate.

In some embodiments, the purification removes at least 50%, 60%, 70%, 80%, 90%, 95%, 96%, 97%, 98%, or 99% non-HCP specific IgGs. In some embodiments, the purification removes at least 99% non-HCP specific IgGs. In some embodiments, the purification removes more than 50%, 60%, 70%, 80%, 90%, 95%, 96%, 97%, 98%, or 99% non-HCP specific IgGs. In some embodiments, the purification removes more than 99% non-HCP specific IgGs. In some embodiments, the polyclonal antibody preparation is substantially free from non-HCP specific IgGs. In some embodiments, the polyclonal antibody preparation contains no more than 0.5%, 1%, 2%, 3%, 5%, 10%, 20%, 30%, 40%, or 50% non-HCP specific IgGs. In some embodiments, the polyclonal antibody preparation contains less than 50%, 40%, 30%, 20%, 10%, 5%, 4%, 3%, 2%, 1%, 0.5% non-HCP specific IgGs.

In one aspect, disclosed herein are methods of making a polyclonal anti-HCP antibody preparation for use in an ELISA for detection of HCPs in a recombinant polypeptide preparation, the method comprising: a) acquiring a sample comprising antibodies, e.g., antisera, from an animal (e.g., a sheep, rabbit, mouse, rat, hamster, goat, etc.) immunized with HCP of a host cell (e.g., a cell line, e.g., a mammalian, rodent, or insect cell or cell line, e.g., a CHO, SP2, NSO host cell); b) separating antibodies from the antisera with by contacting the antisera with a protein A affinity reagent to provide an antibody preparation; c) separating anti-HCP antibody from the antibody preparation by contacting the antibody preparation with an HCP-affinity reagent, thereby producing a polyclonal anti-HCP antibody preparation.

In some embodiments, the purification removes at least 50%, 60%, 70%, 80%, 90%, 95%, 96%, 97%, 98%, or 99% non-HCP specific IgGs. In some embodiments, the purification removes at least 99% non-HCP specific IgGs. In some embodiments, the purification removes more than 50%, 60%, 70%, 80%, 90%, 95%, 96%, 97%, 98%, or 99% non-HCP specific IgGs. In some embodiments, the purification removes more than 99% non-HCP specific IgGs. In some embodiments, the polyclonal antibody preparation is substantially free from non-HCP specific IgGs. In some embodiments, the polyclonal antibody preparation contains no more than 0.5%, 1%, 2%, 3%, 5%, 10%, 20%, 30%, 40%, or 50% non-HCP specific IgGs. In some embodiments, the polyclonal antibody preparation contains less than 50%, 40%, 30%, 20%, 10%, 5%, 4%, 3%, 2%, 1%, 0.5% non-HCP specific IgGs.

In one aspect, disclosed herein are methods of detecting, monitoring, identifying, or quantifying a host cell protein (HCP) (e.g., a CHO HCP) in a sample comprising a recombinant polypeptide, the method comprising: a) providing or obtaining a sample comprising a recombinant polypeptide; b) contacting and incubating the sample with a polyclonal anti-HCP antibody (e.g., an anti-CHO HCP antibody) immobilized to a solid support to form an immobilized antibody-HCP complex, wherein the polyclonal antibody has been produced by any of the methods described herein; c) separating the sample from the immobilized antibody-HCP complex; d) contacting the immobilized antibody-HCP complex with a detectable antibody that binds to GS-CHO HCPs; e) detecting the presence of HCP bound to the antibody using a detection means for the detectable antibody; and f) optionally quantifying the level of HCP detected; g) optionally identifying one of more of the HCP detected; and h) optionally quantifying one or more of the HCP identified.

In one aspect, disclosed herein are methods of detecting, monitoring, identifying, or quantifying a GS-CHO host cell protein (HCP) in a sample comprising a recombinant polypeptide, e.g., therapeutic polypeptide, the method comprising: a) providing or obtaining a sample comprising a recombinant polypeptide; b) incubating the sample with a polyclonal anti-GS-CHO HCP antibody immobilized to a support, e.g., an insoluble or solid support, to form an immobilized antibody-GS-CHO HCP complex; c) separating the sample from the immobilized antibody-GS-CHO HCP complex; d) contacting the immobilized antibody-GS-CHO HCP complex with a detectable reagent, e.g., an antibody that binds to GS-CHO HCPs; e) detecting the presence of GS-CHO HCP bound to the antibody using a detection means for the detectable antibody; and f) optionally quantifying the level of GS-CHO HCP detected; g) optionally identifying one of more of the GS-CHO HCP detected; and h) optionally quantifying one or more of the GS-CHO HCP identified.

In some embodiments, i) the recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin, or ii) the recombinant polypeptide is one disclosed in Tables 1 or 2.

In some embodiments, the recombinant polypeptide is an antibody, e.g., a monoclonal antibody, e.g., a therapeutic antibody.

In some embodiments, i) the sample is derived from a downstream processing step in a production process of the recombinant polypeptide, ii) the sample is derived from an upstream processing step in a production process of the recombinant polypeptide, iii) the sample is derived from a final product of the recombinant polypeptide, or iv) the method comprises two, three, four, five, six, seven, eight, nine, ten, or more than ten samples derived from one or more steps in a production process of the recombinant polypeptide.

In some embodiments, the detectable antibody is: i) directly detectable, ii) amplified by a fluorimetric reagent, or iii) biotinylated and the detection means is avidin or streptavidin-peroxidase and 3,3',5,5'-tetramethyl benzidine.

In one aspect, disclosed herein are methods manufacturing a recombinant polypeptide, e.g., therapeutic polypeptide, drug product, the method comprising: a) providing or obtaining a sample of a recombinant polypeptide preparation; b) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; d) contacting the immobilized antibody-GS-CHO HCP complex with a detectable antibody that binds to GS-CHO HCP; e) quantifying the level of GS-CHO HCP bound to the capture reagent using a detection means for the detectable antibody; and f) processing at least a portion of the preparation as drug product if the level of GS-CHO HCP is below a preselected reference level, optionally wherein processing comprises one or more of: formulating the polypeptide preparation; processing the polypeptide preparation into a drug product; combining the polypeptide preparation with a second component, e.g., an excipient or buffer; changing the concentration of the polypeptide in the preparation; lyophilizing the polypeptide preparation; combining a first and second aliquot of the polypeptide to provide a third, larger, aliquot; dividing the polypeptide preparation into smaller aliquots; disposing the polypeptide preparation into a container, e.g., a gas or liquid tight container; packaging the polypeptide preparation; associating a container comprising the polypeptide preparation with a label (e.g., labeling); shipping or moving the polypeptide preparation to a different location, thereby manufacturing a recombinant polypeptide drug product.

In one aspect, disclosed herein are methods of manufacturing a recombinant polypeptide, e.g., therapeutic polypeptide, drug product, the method comprising: a) culturing a GS-CHO cell cultured under conditions suitable for production, e.g., expression and secretion, of a recombinant polypeptide, b) separating the secreted recombinant polypeptide from the host cell; c) subjected the secreted recombinant polypeptide to one or more purification steps to produce a recombinant polypeptide preparation; d) taking a sample of a recombinant polypeptide preparation; e) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; f) contacting the immobilized antibody-GS-CHO HCP complex with a detectable antibody that binds to GS-CHO HCP; g) quantifying the level of GS-CHO HCP bound to the capture reagent using a detection means for the detectable antibody; and h) processing at least a portion of the preparation as drug product if the level of GS-CHO HCP is below a preselected reference level, optionally wherein the processing comprises one or more of: formulating the polypeptide preparation; processing the polypeptide preparation into a drug product; combining the polypeptide preparation with a second component, e.g., an excipient or buffer; changing the concentration of the polypeptide in the preparation; lyophilizing the polypeptide preparation; combining a first and second aliquot of the polypeptide to provide a third, larger, aliquot; dividing the polypeptide preparation into smaller aliquots; disposing the polypeptide preparation into a container, e.g., a gas or liquid tight container; packaging the polypeptide preparation; associating a container comprising the polypeptide preparation with a label (e.g., labeling); shipping or moving the polypeptide preparation to a different location, thereby manufacturing a recombinant polypeptide drug product.

In some embodiments, the reference level is: i) about 100 ppm (e.g., less than 100, 90, 80, 70, 60, 50, 40, 30, 20, 10, 5, 1 ppm), ii) between 1 ppm and 1000 ppm, iii) at least 1 ppm, 10 pppm, 50 ppm, 100 ppm, 500 ppm, or 1000 ppm, or iv) no greater than 1 ppm, 5 ppm, 10 pppm, 20 ppm, 30 ppm, 40 ppm, 50 ppm, 100 ppm, 500 ppm, or 1000 ppm.

In some embodiments, the level of GS-CHO HCP below the reference level is a specification for commercial release of the drug product, e.g., under Section 351(a) of the Public Health Service (PHS) Act, and, optionally wherein the level of GS-CHO HCP is acquired for one, two, or more samples or batches.

In some embodiments, i) the recombinant polypeptide is a homopolymeric or heteropolymeric polypeptide, e.g., a hormone, growth factor, receptor, antibody, cytokine, receptor ligand, transcription factor or enzyme, preferably an antibody or an antibody fragment, e.g., a human antibody or a humanized antibody or fragment thereof, e.g., a humanized antibody or fragment thereof derived from a mouse, rat, rabbit, goat, sheep, or cow antibody, typically of rabbit origin, or ii) the recombinant polypeptide is one disclosed in Tables 1 or 2.

In some embodiments, the recombinant polypeptide is an antibody, e.g., a monoclonal antibody, e.g., a therapeutic antibody.

In some embodiments, i) the sample is derived from a downstream processing step in a production process of the recombinant polypeptide, ii) the sample is derived from an upstream processing step in a production process of the recombinant polypeptide, iii) the sample is derived from a final product of the recombinant polypeptide, or iv) the method comprises two, three, four, five, six, seven, eight, nine, ten, or more than ten samples derived from one or more steps in a production process of the recombinant polypeptide.

In some embodiments, the detectable antibody is: i) directly detectable, ii) amplified by a fluorimetric reagent, or iii) biotinylated and the detection means is avidin or streptavidin-peroxidase and 3,3',5,5'-tetramethyl benzidine.

In one aspect, disclosed herein are methods of manufacturing a recombinant polypeptide drug product, the method comprising: a) providing or obtaining a sample of a recombinant polypeptide preparation from culture of a GS-CHO cell; b) acquiring a value for the GS-CHO host cell protein (HCP) in the sample, and, c) optionally evaluating the acquired value, e.g., by comparing the acquired value with a reference value; and d) optionally responsive to the evaluation, classifying, selecting, accepting, releasing, processing into a drug product, shipping, moving to a different location, formulating, labeling, packaging, releasing into commerce, selling or offering for sale the preparation, wherein the value is a function of, is proportional to, or was obtained by, the binding of a polyclonal GS-CHO antibody to the sample, thereby manufacturing a recombinant polypeptide drug product.

In some embodiments, the value was determined by any method described herein.

In one aspect, disclosed herein are kits comprising: a) a polyclonal anti-GS-CHO HCP antibody immobilized to a solid support; b) optionally a detectable antibody; c) optionally a wash buffer; and d) optionally a detecting reagent, e.g., a detecting reagent that is the same as the capture reagent or the same as the capture reagent only modified to be amplified by a fluorimetric reagent, and optionally wherein the detecting antibody is biotinylated and the detection means is avidin or streptavidin-peroxidase and 3,3',5,5'-tetramethyl benzidine.

In one aspect, disclosed herein are purified preparations of polyclonal anti-GS-CHO antibody, optionally wherein the anti-GS-CHO antibody is a sheep, goat, horse, rabbit, bovine, murine, hamster, or human antibody.

In some embodiments, the preparation is substantially free from non-HCP specific IgGs, e.g., the preparation contains no more than 0.5%, 1%, 2%, 3%, 5%, 10%, 20%, 30%, 40%, or 50% non-HCP specific IgGs or the preparation contains less than 50%, 40%, 30%, 20%, 10%, 5%, 4%, 3%, 2%, 1%, 0.5% non-HCP specific IgGs.

In one aspect, disclosed herein are methods of determining whether a batch or lot of a recombinant polypeptide drug product meets or satisfies a release specification, wherein the release specification is a preselected reference level of GS-CHO HCP the method comprising: a) providing or obtaining a sample of a recombinant polypeptide preparation; b) contacting and incubating the sample with a polyclonal anti-GS-CHO HCP antibody immobilized to a solid support to form an immobilized antibody-GS-CHO HCP complex; c) separating the sample from the immobilized antibody-GS-CHO HCP complex; d) contacting the immobilized antibody-GS-CHO HCP complex with a detectable antibody that binds to GS-CHO HCP; e) quantifying the level of GS-CHO HCP bound to the capture reagent using a detection means for the detectable antibody; and f) processing at least a portion of the preparation as drug product if the level of GS-CHO HCP meets, satisfies, or is below the release specification, and optionally wherein processing comprises classifying, selecting, accepting, releasing, processing into a drug product, shipping, moving to a different location, formulating, labeling, packaging, releasing into commerce, selling or offering for sale the preparation, thereby determining whether a batch or lot of a recombinant polypeptide drug product meets or satisfies a release specification.

In one aspect, disclosed herein are methods of making a polyclonal anti-HCP antibody preparation, the method comprising: a) acquiring a sample comprising antibodies, e.g., antisera, from an animal (e.g., a sheep, rabbit, mouse, rat, hamster, goat, etc.) immunized with HCP of a host cell (e.g., a cell line, e.g., a mammalian, rodent, or insect cell or cell line, e.g., a CHO, SP2, NSO host cell); and b) separating anti-HCP antibody from the sample, e.g., by contacting the sample with an HCP-affinity reagent, e.g., protein A, and optionally wherein b) comprises: b.1) separating antibodies, e.g., IgG antibodies, from the sample to provide an antibody preparation; and b.2) separating anti-HCP antibody from the antibody preparation, e.g., by contacting the antibody preparation with an HCP-affinity reagent, thereby producing a polyclonal anti-HCP antibody preparation.

In some embodiments, the purification removes: i) at least 50%, 60%, 70%, 80%, 90%, 95%, 96%, 97%, 98%, or 99% non-HCP specific IgGs, e.g., at least 99% non-HCP specific IgGs, or ii) more than 50%, 60%, 70%, 80%, 90%, 95%, 96%, 97%, 98%, or 99% non-HCP specific IgGs, e.g., more than 99% non-HCP specific IgGs.

In some embodiments, the polyclonal antibody preparation is substantially free from non-HCP specific IgGs, e.g., contains no more than 0.5%, 1%, 2%, 3%, 5%, 10%, 20%, 30%, 40%, or 50% non-HCP specific IgGs or contains less than 50%, 40%, 30%, 20%, 10%, 5%, 4%, 3%, 2%, 1%, 0.5% non-HCP specific IgGs

BRIEF DESCRIPTION OF THE DRAWINGS

FIG. 1 depicts an exemplary purification process for sheep GS-CHO HCP antibody.

DETAILED DESCRIPTION

For recombinant biopharmaceutical proteins to be acceptable for administration to human patients, it is important that residual contaminants resulting from the manufacture and purification process are removed from the final biological product. These process contaminants include culture medium proteins, immunoglobulin affinity ligands, viruses, endotoxin, DNA, and host cell proteins (HCPs). HCPs may generate a range of undesirable effects that may impact on the safety profile of a product, including immune response, adjuvant activity, direct biological activity or product interaction/degradation. These host cell contaminants include process-specific HCPs, which are process-related impurities/contaminants in the biologics derived from recombinant DNA technology.

U.S. and foreign regulations often require removal of such contaminants. For example, the U.S. Food and Drug Administration (FDA) requires that biopharmaceuticals intended for in vivo human use should be as free as possible of extraneous immunoglobulin and non-immunoglobulin contaminants, and requires tests for detection and quantitation of potential contaminants, such as HCPs. The International Conference on Harmonization (ICH) provides guidelines on test procedures and acceptance criteria for biotechnological/biological products. The guidelines suggest that for HCPs, a sensitive immunoassay capable of detecting a wide range of protein impurities be utilized. Although there are commercial assays and reagents available to detect immunoglobulins, DNA, endotoxins, viruses, etc., there are currently no commercial reagents or analytical methods available for the detection and quantification of cell line specific GS-CHO HCPs.

The present disclosure provides, inter alia, a robust, sensitive HCP ELISA platform assay and methods of use, to support multiple expression systems, including e.g., mammalian expression systems, e.g., the CHOK1SV expression system. The quality of an HCP ELISA method is defined mainly by 2 parameters (1) limit of quantitation (LOQ), and (2) percentage coverage of the HCPs that could be present as contaminants. Currently available HCP ELISAs provide 200 ng/ml-1000 ng/mg for LOQ and 40%-60% for coverage by spot counting. The ELISA described herein provide an LOQ of 2 ng/mg and 71% coverage by spots matching (which is a better approach than spot counting), satisfying both of these parameters. The platform assay can support HCP detection in different products from a stable cell line and process (e.g., GS-CHO).

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "a cell" can mean one cell or more than one cell.

As used herein, the term "host cell protein" or "HCP" refers to any protein produced or encoded by the organism used to produce a recombinant polypeptide product and unrelated to the intended recombinant product. HCPs are undesirable in the final drug substance.

As used herein, the term "GS-CHO" refers to a Chinese hamster ovary (CHO) cell that expresses a recombinant glutathione synthetase (GS). For example, a CHO-K1SV GS (Lonza Biologics, Inc.).

As used herein, the term "GS-CHO HCP" refers to a host cell protein derived from a GS-CHO cell.

As used herein, the term "endogenous" refers to any material from or naturally produced inside an organism, cell, tissue or system.

As used herein, the term "exogenous" refers to any material introduced to or produced outside of an organism, cell, tissue or system. Accordingly, "exogenous nucleic acid" refers to a nucleic acid that is introduced to or produced outside of an organism, cell, tissue or system. In an embodiment, sequences of the exogenous nucleic acid are not naturally produced, or cannot be naturally found, inside the organism, cell, tissue, or system that the exogenous nucleic acid is introduced into. In one embodiment, the sequences of the exogenous nucleic acids are non-naturally occurring sequences, or encode non-naturally occurring products.

As used herein, the term "heterologous" refers to any material from one species, when introduced to an organism, cell, tissue or system from a different species.

As used herein, the terms "nucleic acid," "polynucleotide," or "nucleic acid molecule" are used interchangeably and refers to deoxyribonucleic acid (DNA) or ribonucleic acid (RNA), or a combination of a DNA or RNA thereof, and polymers thereof in either single- or double-stranded form. The term "nucleic acid" includes, but is not limited to, a gene, cDNA, or an mRNA. In one embodiment, the nucleic acid molecule is synthetic (e.g., chemically synthesized or artificial) or recombinant. Unless specifically limited, the term encompasses molecules containing analogues or derivatives of natural nucleotides that have similar binding properties as the reference nucleic acid and are metabolized in a manner similar to naturally or non-naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

As used herein, the terms "peptide," "polypeptide," and "protein" are used interchangeably, and refer to a compound comprised of amino acid residues covalently linked by peptide bonds, or by means other than peptide bonds. A protein or peptide must contain at least two amino acids, and no limitation is placed on the maximum number of amino acids that can comprise a protein's or peptide's sequence. In one embodiment, a protein may comprise of more than one, e.g., two, three, four, five, or more, polypeptides, in which each polypeptide is associated to another by either covalent or non-covalent bonds/interactions. Polypeptides include any peptide or protein comprising two or more amino acids joined to each other by peptide bonds or by means other than peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others.

As used herein, "product" refers to a molecule, nucleic acid, polypeptide, or any hybrid thereof, that is produced, e.g., expressed, by a cell which has been modified or engineered to produce the product. In one embodiment, the product is a naturally occurring product or a non-naturally occurring product, e.g., a synthetic product. In one embodiment, a portion of the product is naturally occurring, while another portion of the product is non-naturally occurring. In one embodiment, the product is a polypeptide, e.g., a recombinant polypeptide. In one embodiment, the product is suitable for diagnostic or pre-clinical use. In another embodiment, the product is suitable for therapeutic use, e.g., for treatment of a disease. In one embodiment, the product is selected from Table 1 or Table 2. In one embodiment, the modified or engineered cells comprise an exogenous nucleic acid that controls expression or encodes the product. In other embodiments, the modified or engineered cells comprise other molecules, e.g., that are not nucleic acids, that controls the expression or construction of the product in the cell.

In one embodiment, the modification of the cell comprises the introduction of an exogenous nucleic acid comprising a nucleic acid sequence that controls or alters, e.g., increases, the expression of an endogenous nucleic acid sequence, e.g., endogenous gene. In such embodiments, the modified cell produces an endogenous polypeptide product that is naturally or endogenously expressed by the cell, but the modification increases the production of the product and/or the quality of the product as compared to an unmodified cell, e.g., as compared to endogenous production or quality of the polypeptide.

In another embodiment, the modification of the cell comprises the introduction of an exogenous nucleic acid encoding a recombinant polypeptide as described herein. In such embodiments, the modified cell produces a recombinant polypeptide product that can be naturally occurring or non-naturally occurring. In such embodiments, the modified cell produces a recombinant polypeptide product that can also be endogenously expressed by the cell or not. In embodiments where the recombinant polypeptide product is also endogenously expressed by the cell, the modification increases the production of the product and/or the quality of the product as compared to an unmodified cell, e.g., as compared to endogenous production or quality of the polypeptide.

As used herein, "recombinant polypeptide" or "recombinant protein" refers to a polypeptide that can be produced by a cell described herein. A recombinant polypeptide is one for which at least one nucleotide of the sequence encoding the polypeptide, or at least one nucleotide of a sequence which controls the expression of the polypeptide, was formed by genetic engineering (of the cell or of a precursor cell). E.g., at least one nucleotide was altered, e.g., it was introduced into the cell or it is the product of a genetically engineered rearrangement. In an embodiment, the sequence of a recombinant polypeptide does not differ from a naturally occurring isoform of the polypeptide or protein. In an embodiment, the amino acid sequence of the recombinant polypeptide differs from the sequence of a naturally occurring isoform of the polypeptide or protein. In an embodiment, the recombinant polypeptide and the cell are from the same species. In an embodiment, the recombinant polypeptide is endogenous to the cell, in other words, the cell is from a first species and the recombinant polypeptide is native to that first species. In an embodiment, the amino acid sequence of the recombinant polypeptide is the same as or is substantially the same as, or differs by no more than 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 99% from, a polypeptide encoded by the endogenous genome of the cell. In an embodiment, the recombinant polypeptide and the cell are from different species, e.g., the recombinant polypeptide is a human polypeptide and the cell is a non-human, e.g., a rodent, e.g., a CHO, or an insect cell. In an embodiment, the recombinant polypeptide is exogenous to the cell, in other words, the cell is from a first species and the recombinant polypeptide is from a second species. In one embodiment, the polypeptide is a synthetic polypeptide. In one embodiment, the polypeptide is derived from a non-naturally occurring source. In an embodiment, the recombinant polypeptide is a human polypeptide or protein which does not differ in amino acid sequence from a naturally occurring isoform of the human polypeptide or protein. In an embodiment, the recombinant polypeptide differs from a naturally occurring isoform of the human polypeptide or protein at no more than 1, 2, 3, 4, 5, 10, 15 or 20 amino acid residues. In an embodiment, the recombinant polypeptide differs from a naturally occurring isoform of the human polypeptide by no more than 1, 2, 3, 4, 5, 6, 7, 8, 9, 10, or 15% of its amino acid residues.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Downstream processing step" as the term is used herein, refers to any step in the production process of the recombinant polypeptide that follows after/post a chosen separation step, e.g., after/post separation of the cells from the media containing the recombinant protein product.

"Upstream processing step" as the term is used herein, refers to any step in the production process of the recombinant polypeptide that precedes or is prior to a chosen separation step, e.g., prior to separation of the recombinant protein product from cell containing media.

"Final product" as the term is used herein, refers to a recombinant polypeptide substantially purified from other cellular components. In some embodiments, a final product is a recombinant polypeptide that is formulated for storage, shipping, and/or use as a drug.

"Production process" as the term is used herein, refers to a method or series of steps that produces a recombinant polypeptide. In some embodiments, a production process is a manufacturing process designed to produce a recombinant polypeptide. In some embodiments, a production process is a method for purifying a recombinant polypeptide. In some embodiments, a production process further comprises evaluation steps, analysis steps, and/or determination steps based on said evaluation and analysis. In some embodiments, the final product of a production process is a recombinant polypeptide formulated for use as a drug.

The disclosures of each and every patent, patent application, and publication cited herein are hereby incorporated herein by reference in their entirety. While this invention has been disclosed with reference to specific aspects, it is apparent that other aspects and variations of this invention may be devised by others skilled in the art without departing from the true spirit and scope of the invention. The appended claims are intended to be construed to include all such aspects and equivalent variations.

General Description of the Process

The methods described herein may be characterized as an enzyme linked immunosorbant assay (ELISA). The general method of an ELISA and ELISA variations are known to those skilled in the art. The following is a general description of the methods described herein solely to illustrate the timeline of steps involved in the methods. The disclosure should not be limited to or restricted to this description in anyway. The components are merely described for purposes of illustration.

A coating agent (e.g., anti-GS-CHO HCP antibody) is immobilized onto a solid support (e.g., microtiter plate). Once the coating agent has been immobilized on the solid support the remaining binding sites on the solid support are blocked using a blocking buffer (e.g., 0.2% casein in 1×DPBS). The blocking buffer contains a component capable of non-specifically binding to the solid support to saturate the open binding sites, therefore preventing binding of free ligand to any excess sites on the solid support. The specific conditions of the coating and blocking incubation periods are selected to maximize coating of the solid support; and variations are known to those skilled in the art. After coating and blocking of the solid support, the standards and/or samples (e.g., samples being tested for HCPs) to be analyzed are appropriately diluted in a suitable dilution buffer (e.g., 0.2% casein in 1×DPBS) and added to the immobilized support. The specific conditions of the standard/sample incubation period are selected to maximize sensitivity of the assay and minimize dissociation; variations are known to those skilled in the art.

Any non-immobilized standard/sample (e.g., HCP) is removed by washing the solid support with a suitable wash buffer (e.g., 0.05% Tween® 20 in 1×DPBS), a suitable number of times (e.g., 3× with 300 µl). The specific wash buffer and number washes at any wash step are selected to minimize background and maximize sensitivity; and variations are known to those skilled in the art. Any immobilized standard/sample can then be detected either indirectly or directly. For indirect detection, an antibody (primary antibody) against the antigen of interest in the standard/sample (e.g., anti-GS-CHO HCP antibody) is added to the solid support; and the incubation conditions selected to maximize signal amplification. Any non-immobilized antibody is then removed by washing the solid support with a suitable washing buffer, a suitable number of times. An antibody conjugated to a moiety that is detectable by some means (detecting antibody) and capable of binding to the immobilized standard or HCP in sample is then added to the solid support. Any unbound detecting antibody is then removed by washing the solid support with a suitable washing buffer, a suitable number of times. The level of the antigen of interest in the standard/sample (e.g., HCP) bound to the coating agent can be determined using a detection system compatible with the detection antibody employed. A suitable detection means will be known to one of skill in the art.

In the instance direct detection of the antigen of interest in the standard/sample is employed, the primary antibody is conjugated to a moiety that is detectable by some means and is thus also the detecting antibody, i.e., the primary antibody and detecting antibody are the same. Any unbound detecting antibody is then removed by washing the solid support with a suitable washing buffer, a suitable number of times. The level of the antigen of interest in the standard/sample (e.g., HCP) bound to the coating agent can be determined using a detection system compatible with the primary/detection antibody employed. A suitable detection system will be known to one of skill in the art.

The results demonstrate, inter alia, a robust, sensitive HCP ELISA platform assay to support multiple host cell expression systems, including e.g., CHOK1SV expression system and GS-CHO expression system. The improved sensitivity of the ELISA assay is at least about-40-fold, better than a HCP ELISA method not using the polyclonal HCP antibody purified as described herein. During the HCP antibody purification, over 99% of total IgGs showed no immunoresponse to the HCP and were therefore eliminated from the final HCP antibody. As there is no exactly matched standards for quantitation cross the industry and regulation, the sensitivity of HCP assay is assay specific for cell line and process. The methods described herein can be used to generate a robust, sensitive HCP ELISA platform assay for any recombinant host cell, including but not limited to, for example mammalian host cells (e.g., CHO, e.g., GS-CHO), eukaryotic host cell, prokaryotic host cells, insect cell. Additionally, the methods of the invention can be used in conjunction with regulatory requirements for the production of recombinant proteins.

In some embodiments, the HCP ELISA assay of the present invention demonstrates acceptable accuracy, precision, and linearity for robust and reliable HCP detection at concentration ranges comprising 0.1-100, 0.5-100, 1-100, 1.5-100, 2-100, 2.5-100, 3-100, 0.1-90, 0.5-90, 1-90, 1.5-90, 2-90, 2.5-90, 3-90, 0.1-80, 0.5-80, 1-80, 1.5-80, 2-80, 2.5-80, 3-80, 0.1-70, 0.5-70, 1-70, 1.5-70, 2-70, 2.5-70, 3-70, 0.1-60, 0.5-60, 1-60, 1.5-60, 2-60, 2.5-60, or 3-60 ng/ml. In some embodiments, the HCP ELISA assay demonstrates acceptable accuracy, precision, and linearity for robust and reliable HCP detection at a concentration range comprising 2 through 60 ng/ml. In some embodiments, the HCP ELISA assay demonstrates acceptable accuracy, precision, and linearity for robust and reliable HCP detection at a concentration range comprising 3 through 80 ng/ml. In some embodiments, the limit of detection of the HCP ELISA assay of the present invention is 0.1, 0.2, 0.3, 0.4, 0.5, 0.6, 0.7, 0.8, 0.9, 1, 2, 3, 4, 5, 6, 7, 8, 9, or 10 ng/ml. In some embodiments, the limit of detection of the HCP ELISA assay of the present invention is 0.5 ng/ml. In some embodiments, the limit of detection of the HCP ELISA assay of the present invention is 2 ng/ml. In some embodiments, the limit of quantitation of the HCP ELISA assay of the present invention is 0.1, 0.2, 0.3, 0.4, 0.5, 0.6, 0.7, 0.8, 0.9, 1, 2, 3, 4, 5, 6, 7, 8, 9, or 10 ng/ml. In some embodiments, the limit of detection of the HCP ELISA assay of the present invention is 3 ng/ml.

ANTI-GS-CHO HCP ANTIBODIES

The methods described herein can provide an anti-GS-CHO HCP antibody for the detection of HCP. Anti-GS-CHO HCP antibodies can be made by standard molecular biology techniques. The antibodies can be derived from any species. The antibodies can be monoclonal or polyclonal or any variation of an "antibody" described herein. In some embodiments, the antibody is a polyclonal antibody. In some embodiments, the antibody is a polyclonal antibody made in sheep. The antibodies can be directly detectable through the attachment of a detectable label, e.g., a chemical modification, enzyme conjugation, fluorescent dye labeling, luminescence labeling, etc. The antibodies can also not be directly detectable, and require a secondary means for detection. Antibodies with these various properties can be purchased or made by standard molecular biology techniques.

SAMPLES

Samples can include, but are not limited to samples taken from a cell culture at any period during recombinant protein production, e.g., any point during upstream or downstream processing. For example, samples may be taken from a cell culture (e.g., prior to separation of the recombinant protein product). Samples may be taken during the downstream processing process, e.g., post separation of the cells from the media containing the recombinant protein product. A sample may be taken at any and at multiple points during a purification process. A sample can include a sample of the final product. Accordingly, samples may include both in process products (prior to final formulation) and final products (e.g., final formulated products post all purification steps).

SOLID SUPPORT

Solid supports can include any surface to which a coating agent, e.g., anti-GS-CHO HCP antibody, or equivalent thereof can be immobilized on. Solid supports used for immobilization can be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assays plates or test tubes manufactured from polyethylene, polypropylene, polystyrene, and the like including 96-well microtiter plates, as well as particulate materials such as filter paper, agarose, cross-linked dextran, and other polysaccharides. Alternatively, reactive water insoluble matrices such as cyanogens bromide-activated carbohydrates are suitably employed for coating reagent immobilization. The immobilized coating agent can be coated on a microtiter plate, for instance a multi-well microtiter plate that can be used to analyze several samples at one time. Solid support surfaces can also include but are not limited to, a membrane, e.g., a nitrocellulose membrane, a polytetraluorethylene membrane, cellulose acetate membrane, cellulose nitrate membrane, a solid surface coated with molecules containing hydrophobic groups, a solid surface coated with molecules containing hydrophilic groups. Solid support surfaces can be in the form of a microtiter plate, e.g., a polystyrene microtiter plate, cell culture plate, or any variation thereof.

CAPTURE REAGENT

The term "capture reagent" refers to an antibody which binds directly to the antigen of interest (e.g., GS-CHO HCP). The capture antibody can also be a detecting antibody with protein modification, e.g., biotinylation. The antibodies can be derived from different species, including but not limited to, human, rabbit, mouse, rat, sheep, goat, chicken, human, horse, dog, cat, hamster, monkey, chimpanzee, ovine, equine, porcine, bovine, primate, etc. In some embodiments, the primary antibody is an anti-GS-CHO HCP antibody produced in sheep and affinity purified.

DETECTING REAGENT

The term "detecting reagent" or "detection reagent" refers to a labeled antibody used to detect an "antigen" or "antibody". The detecting antibody can also be a primary antibody. The antibodies can be derived from different species, including but not limited to, human, rabbit, mouse, rat, sheep, goat, chicken, human, horse, dog, cat, hamster, monkey, chimpanzee, ovine, equine, porcine, bovine, primate, etc. The label used on the detecting antibody can be any detectable functionality that does not interfere with the binding of HCP to the antibody. Examples of suitable labels are those numerous labels known for use immunoassays, including moieties that may be detected directly, such as fluorochrome, chemiluminscent, and radioactive labels, as well as moieties, such as enzymes, that must be reacted or derivatized to be detected. Suitable labeling methods that can be used in the present invention include, but are not limited to, isotope labeling, chemical modification, enzyme conjugation, fluorescent dye labeling, luminescence labeling, and other labeling methods commonly known to those skilled in the art.

Commercially available antibodies to a wide variety of antigens are known in the art. Those skilled in the art will be aware of a variety of labeling methods for an antibody or other detection agent. Labeling methods include but are not limited to, an enzyme such as horse radish peroxide (HRP), alkaline phosphatase (AP), beta-galactosidase, glucoamylase, lysozyme, saccharide oxidases, e.g., glucose oxidase, glactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-β-galactosidase with MUG, spin labels, bacteriophage labels, stable free radicals, or other enzymes and the like. A detection agent can also be labeled with radioactive isotopes, e.g., $^{125}I$, $^{32}P$, $^{14}C$, $^{3}H$, and $^{131}I$, or other isotope. Fluorescent labels can include but are not limited to fluorophores such as rare earth cheats or fluorescein and its derivatives, rhodamine and its derivatives, dansyl, umbelliferone, luceriferases, e.g., firefly luciferase and bacterial luciferase (U.S. Pat. No. 4,737,456), luciferin, fluorescin isothiocynate (FITC), rhodamine, Texas Red, Alexa488, Cy5, Cy3, Alexa610, 7-AAD, propidium iodide, Cy7, phycoerythrin, etc. A detection agent can be labeled by a fluorochrome (a fluorescent dye) that can be detected by fluorescent plate reader, a fluorescent microscope, a fluorometer, a camera, or scanner. A detection agent can also be labeled by a lumichrome which can be detected by luminescence methods. Alternatively a detection agent can be labeled biotin, which can bind to avidin or streptavidin. Avidin or streptavidin can be used as detection agents which can bind to biotin, biotinylated antibodies, or biotinylated polypeptides.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and 3,645,090 (enzymes); Hunter et al. Nature 144:945 (1962); David et al. Biochemistry 13:1014-1021 (1974); Pain et al. J. Immunol. Methods 40:219-230 (1981); and Nygren J. Histochem. and Cytochem. 30:407-412 (1982). Preferred labels herein are fluorescent to increase amplification and sensitivity to 8 pg/ml, more preferably biotin with streptavidin-β-galactosidase and MUG for amplifying the signal.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. Langone and H. Van Vunakis, Vol. 73 (Academic Press, New York, N.Y., 1981), pp. 147-166.

DETECTION SYSTEM

The term "detection system" refers to a means which can be used to give a readout comprising information related to the quantity or relative amount of a protein or agent in a sample. The choice of a detection system depends on the choice of the detection antibody used. For example, if a detecting antibody is labeled with an enzyme, in which a chemical reaction can result in color or a chemiluminescence signal; the detection system may include a suitable substrate and any necessary reagents associated with the chemical reaction and a means of detecting the chemical reaction, for example, visual inspection, a device capable of detecting the signal, e.g., an absorbance plate reader, a chemiluminescence plate reader, CCD camera, etc; alternatively, if the detection antibody is fluorescently labeled, a fluorescence microscope, a fluorescence plate reader, a fluorescence cell sorter, a fluorescence scanner, camera, etc. may be used; alternatively, if the detecting antibody is isotope labeled, X ray film or other isotope sensitive material may be used.

Those skilled in the art will be aware of different detection systems suitable for use. These detection systems can include, for example, detection systems using chromogenic reactions of reporter enzymes such as horse radish peroxidase (HRP) or alkaline phoshatase (AP) or the like. The reporter enzymes can use different substrates for chromogenic detection, for example, HRP can use 4 CN (4-chloro-1-napthol), DAB/NiCl$_2$ (3,3'-diaminobenzidine/NiCl$_2$) or TMB as substrates for chromogenic detection. Fluorescent labels include but are not limited to fluorescin isothiocynate (FITC), rhodamine, Texas Red, Alexa488, Cy5, Cy3, Alexa610, 7-AAD, propidium iodide, Cy7, phycoerythrin, etc. Various and appropriate stopping agents can be used to end a detection reaction. The specific stopping agent used will depend on the detection agent used and will be known to one of skill in the art. For example, 1M sulfuric acid can be used as a stopping substrate for detection systems using the horse radish peroxidase enzyme.

BLOCKING BUFFERS

Blocking buffers used to block any remaining binding sites on the solid support post incubation with the coating agent can be used. Examples of blocking buffers include but are not limited to, casein, e.g., casein in 1×PBS, 0.1-1% casein in 1×PBS, 0.1-0.5% casein in 1×PBS, 0.2% casein in 1×PBS; BSA, e.g., BSA in 1×PBS, e.g., 1% BSA in 1×PBS, 1-10% BSA in 1×PBS, 1-20% BSA in 1×PBS, 1-50% BSA in 1×PBS; non-fat milk, fish gelatin, or other chemical reagent. Any of the reagents described above or other suitable chemical reagent can be diluted in any suitable buffer, e.g., phosphate buffered saline (PBS) or tris buffered saline (TBS).

Wash buffers may be used to remove unbound components at various steps. Examples of wash buffers include but are not limited to, casein, e.g., casein in 1×PBS, 0.1-1% casein in 1×PBS, 0.1-0.5% casein in 1×PBS, 0.2% casein in 1×PBS; BSA, e.g., BSA in 1×PBS, e.g., 1% BSA in 1×PBS, 1-10% BSA in 1×PBS, 1-20% BSA in 1×PBS, 1-50% BSA in 1×PBS; BSA in 1×PBS containing Tween® 20, e.g., BSA in 1×PBS containing 0.05% Tween® 20, 1% BSA in 1×PBS containing 0.05% Tween® 20, 1% BSA in 1×PBS containing 0.05-1% Tween® 20; Tween® 20, e.g., Tween® 20 in 1×PBS, e.g., 0.05% Tween® 20 in 1×PBS; non-fat milk, casein, fish gelatin, or other chemical reagent. Washing buffers can include any of the following BSA, non-fat milk, casein, fish gelatin, or other chemical agent in solution with Triton X 100 or Tween® 20 or the like. These solutions can be diluted in any suitable buffer, including but not limited to phosphate buffered saline (PBS), tris-buffered saline (TBS).

Wash steps can be carried out multiple times, and will depend on the wash buffer employed. For example, washing steps can be repeated once, twice, three, four, five, six, seven, eight, nine, ten, or more than ten times at a given wash period. One of skill in the art will be able to determine the number of wash steps necessary based on the wash buffer used and other experimental conditions.

Buffers used to dilute any standards, samples, antibodies, or detection agents will be known to those skilled in the art and can include but are not limited to casein, e.g., casein in 1×PBS, 0.1-1% casein in 1×PBS, 0.1-0.5% casein in 1×PBS, 0.2% casein in 1×PBS; BSA, e.g., BSA in 1×PBS, e.g., 1% BSA in 1×PBS, 1-10% BSA in 1×PBS, 1-20% BSA in 1×PBS, 1-50% BSA in 1×PBS; non-fat milk, casein, fish gelatin, or other chemical reagent. In some instances the buffer used to dilute any standards, samples, antibodies, or detection agents will be the same agent used as a blocking buffer.

INCUBATION TIME PERIODS AND TEMPERATURES

Appropriate incubation periods for various steps can be determined by one of skill in the art. The time period for a specific incubation step may be altered due to a change in the temperature of the incubation step, and likewise a change in the time of an incubation step may necessitate a change in the temperature of the incubation step. The coating step may be carried out for example, overnight at or about 4° C., overnight at or about 2-10° C., 4 hours at or about 37° C., 2-4 hours at or about 37° C., 1-4 hours at or about 37° C., 4 hours at or about 32° C., 2-4 hours at or about 32° C., 1-4 hours at or about 32° C. The blocking step may be carried out for example, for 1 hour at or about 32° C.; 1-2 hours at or about 32° C.; overnight at or about 4° C. The standard/sample incubation step can be carried out for example, for 2 hours at or about 32° C.; 1-2 hours at or about 32° C.; overnight at or about 4° C. The primary antibody or primary/detecting antibody incubation step may be carried out for example, for 1 hour at or about 32° C.; 1-2 hours at or about 32° C.; overnight at or about 4° C. The incubation period and temperature of any detecting system will be dependent on the exact detecting antibody employed, and will be known to those skilled in the art.

KITS

Kits comprising one or more components useful for performing the methods described herein can include but are not limited to, any necessary components, reagents, or materials necessary to perform methods described herein, and/or instructions for performing the methods described herein. The kit can optionally include any additional washing agents, incubation containers, solid support surfaces, and the like for carrying out the methods described herein.

The kit may comprise kit a solid support for the coating agents, which may be provided as a separate element or on which the coating agents are already immobilized. Hence, the coating agent in the kit may be immobilized on a solid support, or they may be immobilized on such support that is included with the kit or provided separately from the kit. The coating agents may be coated on a microtiter plate. The primary antibody may be unlabeled or labeled. The primary antibody may be labeled and also be in the detecting antibody. Where the label is an enzyme, the kit may include substrates and cofactors required by the enzyme, and where the label is a fluorophore, the kit may include a dye precursor that provides the detectable chromophore. The kit may also contain instructions for carrying out the assay, and/or a reference standard, as well as other additives such as stabilizers, washing and incubation buffers, and the like.

PRODUCTS AND NUCLEIC ACIDS ENCODING THEM

Provided herein are methods for identifying, selecting, or making a cell or cell line capable of producing a product. The products encompassed by the present disclosure include, but are not limited to, molecules, nucleic acids, polypeptides (e.g., recombinant polypeptides), or hybrids thereof, that can be produced by, e.g., expressed in, a cell. In some embodiments, the cells are engineered or modified to produce the product. Such modifications include the introducing molecules that control or result in production of the product. For example, a cell is modified by introducing an exogenous nucleic acid that encodes a polypeptide, e.g., a recombinant polypeptide, and the cell is cultured under conditions suitable for production, e.g., expression and secretion, of the polypeptide, e.g., recombinant polypeptide. In another example, a cell is modified by introducing an exogenous nucleic acid that controls, e.g., increases, expression of a polypeptide that is endogenously expressed by the cell, such that the cell produces a higher level or quantity of the polypeptide than the level or quantity that is endogenously produced, e.g., in an unmodified cell.

In embodiments, the cell or cell line identified, selected, or generated by the methods described herein produces a product, e.g., a recombinant polypeptide, useful in the treatment of a medical condition, disorder or disease. Examples of medical conditions, disorders or diseases include, but are not limited to, metabolic disease or disorders (e.g., metabolic enzyme deficiencies), endocrine disorders (e.g., hormone deficiencies), haemostasis, thrombosis, hematopoietic disorders, pulmonary disorders, gastro-intestinal disorders, immunoregulation (e.g., immunodeficiency), infertility, transplantation, cancer, and infectious diseases.

In some embodiments, the product is an exogenous protein, e.g., a protein that is not naturally expressed by the cell. The product can be a therapeutic protein or a diagnostic protein, e.g., useful for drug screening. The therapeutic or diagnostic protein can be an antibody molecule, e.g., an antibody or an antibody fragment, a fusion protein, a hormone, a cytokine, a growth factor, an enzyme, a glycoprotein, a lipoprotein, a reporter protein, a therapeutic peptide, or a structural and/or functional fragment or hybrid of any of these.

In one embodiment, the product, e.g., recombinant polypeptide, is an antibody molecule. Products encompassed herein comprise diagnostic and therapeutic antibody molecules. A diagnostic antibody molecule includes an antibody, e.g., a monoclonal antibody or antibody fragment thereof, useful for imaging techniques. A therapeutic antibody molecule is suitable for administration to subjects, e.g., for treatment or prevention of a disease or disorder.

An antibody molecule is a protein, or polypeptide sequence derived from an immunoglobulin molecule which specifically binds with an antigen. In an embodiment, the antibody molecule is a full-length antibody or an antibody fragment. Antibodies and multiformat proteins can be polyclonal or monoclonal, multiple or single chain, or intact immunoglobulins, and may be derived from natural sources or from recombinant sources. Antibodies can be tetramers of immunoglobulin molecules. In an embodiment, the antibody is a monoclonal antibody. The antibody may be a human or humanized antibody. In one embodiment, the antibody is an IgA, IgG, IgD, or IgE antibody. In one embodiment, the antibody is an IgG1, IgG2, IgG3, or IgG4 antibody.

"Antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen. Examples of antibody fragments include, but are not limited to, Fab, Fab', F(ab')$_2$, and Fv fragments, scFv antibody fragments, linear antibodies, single domain antibodies such as sdAb (either VL or VH), camelid VHH domains, and multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can also be grafted into scaffolds based on polypeptides such as a fibronectin type III (Fn3)(see U.S. Pat. No. 6,703,199, which describes fibronectin polypeptide minibodies).

Exemplary products, e.g., polypeptides, e.g., recombinant polypeptides, produced in the methods or cells described herein are provided in the tables below.

TABLE 1

Exemplary Products

| Therapeutic Product type | Product | Trade Name |
| --- | --- | --- |
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-γ1b (IFN γ) | Actimmune |
| | Aldesleukin (interleukin 2(IL2), epidermal theymocyte activating factor; ETAF | Proleukin |

TABLE 1-continued

Exemplary Products

| Therapeutic Product type | Product | Trade Name |
|---|---|---|
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF receptor/Fc fusion) | Enbrel |
| | Infliximab (TNFα chimeric mAb) | Remicade |
| | Alefacept (CD2 fusion protein) | Amevive |
| | Efalizumab (CD11a mAb) | Raptiva |
| | Natalizumab (integrin α4 subunit mAb) | Tysabri |
| | Eculizumab (C5mAb) | Soliris |
| | Muromonab-CD3 | Orthoclone, OKT3 |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In another embodiment, the product is a bispecific molecule. Bispecific molecules, as described herein, include molecules that can bind to two or more distinct antigens or targets. In an embodiment, a bispecific molecule comprises antibody fragments. In one embodiment, the bispecific molecule comprises a bispecific antibody, a bispecific antibody fusion protein, or a bispecific antibody conjugate, a Bi-specific T cell Engager (BiTE) molecule, a Dual Affinity Re-Targeting (DART) Molecule, a Dual Action Fab (DAF) molecule, a nanobody, or other arrangement of antibody fragments resulting in a molecule having the ability to recognize or bind to two distinct antigens.

TABLE 2

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| Catumaxomab (Reniovab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |

TABLE 2-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| MGD007 (Macrogenics) | DART | CD3, gpA33 | Retargeting of T cells to tumor | Phase I | Colorectal cancer |
| MGD011 (Macrogenics) | DART | CD 19, CD3 | | | |
| SCORPION (Emergent Biosolutions, Trubion) | BsAb | CD3, CD 19 | Retargeting of T cells to tumor | | |
| AFM11 (Affimed Therapeutics) | TandAb | CD3, CD 19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tubingen) | Tandem scFv | CD28, MAPG | Retargeting of T cells to tumor | Phase II | Metastatic melanoma |
| IMCgp100 (Immunocore) | ImmTAC | CD8, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |

TABLE 2-continued

Exemplary Products, e.g., Bispecific Molecules

| BsAb (other names, sponsoring organizations) | BsAb format | Targets | Proposed mechanisms of action | Development stages | Diseases (or healthy volunteers) |
|---|---|---|---|---|---|
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKE, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

Other exemplary therapeutic or diagnostic proteins include, but are not limited to any protein described in Tables 1-10 of Leader et al., "Protein therapeutics: a summary and pharmacological classification", Nature Reviews Drug Discovery, 2008, 7:21-39 (incorporated herein by reference); or any conjugate, variant, analog, or functional fragment of the recombinant polypeptides described herein.

Other recombinant products include non-antibody scaffolds or alternative protein scaffolds, such as, but not limited to: DARPins, affibodies and adnectins. Such non-antibody scaffolds or alternative protein scaffolds can be engineered to recognize or bind to one or two, or more, e.g., 1, 2, 3, 4, or 5 or more, different targets or antigens.

Also provided herein are nucleic acids, e.g., exogenous nucleic acids that encode the products, e.g., polypeptides, e.g., recombinant polypeptides described herein. The nucleic acid sequences coding for the desired recombinant polypeptides can be obtained using recombinant methods known in the art, such as, for example by screening libraries from cells expressing the desired nucleic acid sequence, e.g., gene, by deriving the nucleic acid sequence from a vector known to include the same, or by isolating directly from cells and tissues containing the same, using standard techniques. Alternatively, the nucleic acid encoding the recombinant polypeptide can be produced synthetically, rather than cloned. Recombinant DNA techniques and technology are highly advanced and well established in the art. Accordingly, the ordinarily skilled artisan having the knowledge of the amino acid sequence of a recombinant polypeptide described herein can readily envision or generate the nucleic acid sequence that would encode the recombinant polypeptide.

In some embodiments, the exogenous nucleic acid controls the expression of a product that is endogenously expressed by the host cell. In such embodiments, the exogenous nucleic acid comprises one or more nucleic acid sequences that increase the expression of the endogenous product (also referred to herein as "endogenous product transactivation sequence"). For example, the nucleic acid sequence that increases the expression of an endogenous product comprises a constitutively active promoter or a promoter that is stronger, e.g., increases transcription at the desired site, e.g., increases expression of the desired endogenous gene product. After introduction of the exogenous nucleic acid comprising the endogenous product transactivation sequence, said exogenous nucleic acid is integrated into the chromosomal genome of the cell, e.g., at a preselected location proximal to the genomic sequence encoding the endogenous product, such that the endogenous product transactivation sequence increases the transactivation or expression of the desired endogenous product. Other methods for modifying a cell, e.g., introducing an exogenous nucleic acid, for increasing expression of an endogenous product is described, e.g., in U.S. Pat. No. 5,272,071; hereby incorporated by reference in its entirety.

The expression of a product described herein is typically achieved by operably linking a nucleic acid encoding the recombinant polypeptide or portions thereof to a promoter, and incorporating the construct into an expression vector. The vectors can be suitable for replication and integration eukaryotes or prokaryotes. Typical cloning vectors contain other regulatory elements, such as transcription and translation terminators, initiation sequences, and promoters useful for regulation of the expression of the desired nucleic acid sequence.

The nucleic acid sequences described herein encoding a product, e.g., a recombinant polypeptide, or comprising a nucleic acid sequence that can control the expression of an endogenous product, can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. In embodiments, the expression vector may be provided to a cell in the form of a viral vector. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193). Vectors derived from viruses are suitable tools to achieve long-term gene transfer since they allow long-term, stable integration of a transgene and its propagation in daughter cells.

A vector may also include, e.g., a signal sequence to facilitate secretion, a polyadenylation signal and transcription terminator (e.g., from Bovine Growth Hormone (BGH) gene), an element allowing episomal replication and replication in prokaryotes (e.g. SV40 origin and ColE1 or others known in the art) and/or elements to allow selection, e.g., a selection marker or a reporter gene.

In one embodiment, the vector comprising a nucleic acid sequence encoding a polypeptide, e.g., a recombinant polypeptide, further comprises a promoter sequence responsible for the recruitment of polymerase to enable transcription initiation for expression of the polypeptide, e.g., the recombinant polypeptide. In one embodiment, promoter sequences suitable for the methods described herein are usually associated with enhancers to drive high amounts of transcription and hence deliver large copies of the target exogenous mRNA. In an embodiment, the promoter comprises cytomegalovirus (CMV) major immediate early promoters (Xia, Bringmann et al. 2006) and the SV40 promoter (Chernajovsky, Mory et al. 1984), both derived from their namesake viruses or promoters derived therefrom. Several other less common viral promoters have been successfully employed to drive transcription upon inclusion in an expression vector including Rous Sarcoma virus long terminal repeat (RSV-LTR) and Moloney murine leukaemia virus (MoMLV) LTR (Papadakis, Nicklin et al. 2004). In another embodiment, specific endogenous mammalian promoters can be utilized to drive constitutive transcription of a gene of interest (Pontiller, Gross et al. 2008). The CHO specific Chinese Hamster elongation factor 1-alpha (CHEF1α) promoter has provided a high yielding alternative to viral based sequences (Deer, Allison 2004). In addition to promoters, the vectors described herein further comprise an enhancer region as described above; a specific nucleotide motif region, proximal to the core promoter, which can recruit transcription factors to upregulate the rate of transcription (Riethoven 2010). Similar to promoter sequences, these regions are often derived from viruses and are encompassed within the promoter sequence such as hCMV and SV40 enhancer sequences, or may be additionally included such as adenovirus derived sequences (Gaillet, Gilbert et al. 2007).

In one embodiment, the vector comprising a nucleic acid sequence encoding a product, e.g., a polypeptide, e.g., a recombinant polypeptide, described herein further comprises a nucleic acid sequence that encodes a selection marker. In one embodiment, the selectable marker comprises glutamine synthetase (GS); dihydrofolate reductase (DHFR) e.g., an enzyme which confers resistance to methotrexate (MTX); or an antibiotic marker, e.g., an enzyme that confers resistance to an antibiotic such as: hygromycin, neomycin (G418), zeocin, puromycin, or blasticidin. In another embodiment, the selection marker comprises or is compatible with the Selexis selection system (e.g., SUREtechnology Platform™ and Selexis Genetic Elements™, commercially available from Selexis SA) or the Catalant selection system.

In one embodiment, the vector comprising a nucleic acid sequence encoding a recombinant product described herein comprises a selection marker that is useful in identifying a cell or cells comprise the nucleic acid encoding a recombinant product described herein. In another embodiment, the selection marker is useful in identifying a cell or cells that comprise the integration of the nucleic acid sequence encoding the recombinant product into the genome, as described herein. The identification of a cell or cells that have integrated the nucleic acid sequence encoding the recombinant protein can be useful for the selection and engineering of a cell or cell line that stably expresses the product.

Suitable vectors for use are commercially available, and include vectors associated with the GS Expression System™, GS Xceed™ Gene Expression System, or Potelligent® CHOK1SV technology available from Lonza Biologics, Inc, e.g., vectors as described in Fan et al., *Pharm. Bioprocess.* (2013); 1(5):487-502, which is incorporated herein by reference in its entirety. GS expression vectors comprise the GS gene, or a functional fragment thereof (e.g., a GS mini-gene), and one or more, e.g., 1, 2, or 3, or more, highly efficient transcription cassettes for expression of the gene of interest, e.g., a nucleic acid encoding a recombinant polypeptide described herein. A GS mini-gene comprises, e.g., consists of, intron 6 of the genomic CHO GS gene. In one embodiment, a GS vector comprises a GS gene operably linked to a SV40L promoter and one or two polyA signals. In another embodiment, a GS vector comprises a GS gene operably linked to a SV40E promoter, SV40 splicing and polyadenylation signals. In such embodiments, the transcription cassette, e.g., for expression of the gene of interest or recombinant polypeptide described herein, includes the hCMV-MIE promoter and 5' untranslated sequences from the hCMV-MIE gene including the first intron. Other vectors can be constructed based on GS expression vectors, e.g., wherein other selection markers are substituted for the GS gene in the expression vectors described herein.

Vectors suitable for use in the methods described herein include, but are not limited to, other commercially available vectors, such as, pcDNA3.1/Zeo, pcDNA3.1/CAT, pcDNA3.3TOPO (Thermo Fisher, previously Invitrogen); pTarget, HaloTag (Promega); pUC57 (GenScript); pFLAG-CMV (Sigma-Aldrich); pCMV6 (Origene); pEE12 or pEE14 (Lonza Biologics), or pBK-CMV/pCMV-3Tag-7/pCMV-Tag2B (Stratagene).

CELLS AND CELL CULTURE

In embodiments, the cell is a mammalian cell. In other embodiments, the cell is a cell other than a mammalian cell. In an embodiment, the cell is a mouse, rat, Chinese hamster, Syrian hamster, monkey, ape, dog, horse, ferret, or cat. In embodiments, the cell is a mammalian cell, e.g., a human cell or a rodent cell, e.g., a hamster cell, a mouse cell, or a rat cell. In another embodiment, the cell is from a duck, parrot, fish, insect, plant, fungus, or yeast. In one embodiment, the cell is an Archaebacteria. In an embodiment, the cell is a species of Actinobacteria.

In one embodiment, the cell is a Chinese hamster ovary (CHO) cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

In one embodiment, the cell is a Chinese hamster ovary (CHO) cell. In one embodiment, the cell is a CHO-K1 cell, a CHO-K1 SV cell, a CHO-GSKO cell, a CHOXceed cell. The CHO GS knock-out cell (e.g., GS-CHO cell) is, for example, a CHO-K1SV GS knockout cell (Lonza Biologics, Inc.). The CHO FUT8 knockout cell is, for example, the Potelligent® CHOK1 SV (Lonza Biologics, Inc.).

In another embodiment, the cell is a Hela, HEK293, HT1080, H9, HepG2, MCF7, Jurkat, NIH3T3, PC12, PER.C6, BHK (baby hamster kidney cell), VERO, SP2/0, NS0, YB2/0, Y0, EB66, C127, L cell, COS, e.g., COS1 and COST, QC1-3, CHOK1, CHOK1SV, Potelligent CHOK1SV, CHO GS knockout, CHOK1SV GS-KO, CHOS, CHO DG44, CHO DXB11, and CHOZN, or any cells derived therefrom. In one embodiment, the cell is a stem cell. In one embodiment, the cell is a differentiated form of any of the cells described herein. In one embodiment, the cell is a cell derived from any primary cell in culture.

In an embodiment, the cell is any one of the cells described herein that comprises an exogenous nucleic acid encoding a recombinant polypeptide, e.g., expresses a recombinant polypeptide, e.g., a recombinant polypeptide selected from Table 1 or 2.

In an embodiment, the cell culture is carried out as a batch culture, fed-batch culture, draw and fill culture, or a continuous culture. In an embodiment, the cell culture is a suspension culture. In one embodiment, the cell or cell culture is placed in vivo for expression of the recombinant polypeptide, e.g., placed in a model organism or a human subject.

In one embodiment, the culture media is free of serum. Serum-free and protein-free media are commercially available, e.g., Lonza Biologics.

Suitable media and culture methods for mammalian cell lines are well-known in the art, as described in U.S. Pat. No. 5,633,162 for instance. Examples of standard cell culture media for laboratory flask or low density cell culture and being adapted to the needs of particular cell types are for instance: Roswell Park Memorial Institute (RPMI) 1640 medium (Morre, G., The Journal of the American Medical Association, 199, p. 519 f. 1967), L-15 medium (Leibovitz, A. et al., Amer. J. of Hygiene, 78, 1p. 173 ff, 1963), Dulbecco's modified Eagle's medium (DMEM), Eagle's minimal essential medium (MEM), Ham's F12 medium (Ham, R. et al., Proc. Natl. Acad. Sc. 53, p288 ff. 1965) or Iscoves' modified DMEM lacking albumin, transferrin and lecithin (Iscoves et al., J. Exp. med. 1, p. 923 ff., 1978). For instance, Ham's F10 or F12 media were specially designed for CHO cell culture. Other media specially adapted to CHO cell culture are described in EP-481 791. It is known that such culture media can be supplemented with fetal bovine serum (FBS, also called fetal calf serum FCS), the latter providing a natural source of a plethora of hormones and growth factors. The cell culture of mammalian cells is nowadays a routine operation well-described in scientific textbooks and manuals, it is covered in detail e.g. in R. Ian Fresney, Culture of Animal cells, a manual, 4th edition, Wiley-Liss/N.Y., 2000.

Other suitable cultivation methods are known to the skilled artisan and may depend upon the recombinant polypeptide product and the host cell utilized. It is within the skill of an ordinarily skilled artisan to determine or optimize conditions suitable for the expression and production of the recombinant polypeptide to be expressed by the cell.

In one aspect, the cell or cell line comprises an exogenous nucleic acid that encodes a product, e.g., a recombinant polypeptide. In an embodiment, the cell or cell line expresses the product, e.g., a therapeutic or diagnostic product. Methods for genetically modifying or engineering a cell to express a desired polypeptide or protein are well known in the art, and include, for example, transfection, transduction (e.g., viral transduction), or electroporation.

Physical methods for introducing a nucleic acid, e.g., an exogenous nucleic acid or vector described herein, into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, Molecular Cloning: A Laboratory Manual, volumes 1-4, Cold Spring Harbor Press, NY).

Chemical means for introducing a nucleic acid, e.g., an exogenous nucleic acid or vector described herein, into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In embodiments, the integration of the exogenous nucleic acid into a nucleic acid of the host cell, e.g., the genome or chromosomal nucleic acid of the host cell is desired. Methods for determining whether integration of an exogenous nucleic acid into the genome of the host cell has occurred can include a GS/MSX selection method. The GS/MSX selection method uses complementation of a glutamine auxotrophy by a recombinant GS gene to select for high-level expression of proteins from cells. Briefly, the GS/MSX selection method comprises inclusion of a nucleic acid encoding glutamine synthetase on the vector comprising the exogenous nucleic acid encoding the recombinant polypeptide product. Administration of methionine sulfoximine (MSX) selects cells that have stably integrated into the genome the exogenous nucleic acid encoding both the recombinant polypeptide and GS. As GS can be endogenously expressed by some host cells, e.g., CHO cells, the concentration and duration of selection with MSX can be optimized to identify high producing cells with stable integration of the exogenous nucleic acid encoding the recombinant polypeptide product into the host genome. The GS selection and systems thereof is further described in Fan et al., *Pharm. Bioprocess.* (2013); 1(5):487-502, which is incorporated herein by reference in its entirety.

Other methods for identifying and selecting cells that have stably integrated the exogenous nucleic acid into the host cell genome can include, but are not limited to, inclusion of a reporter gene on the exogenous nucleic acid and assessment of the presence of the reporter gene in the cell, and PCR analysis and detection of the exogenous nucleic acid.

In one embodiment, the cells selected, identified, or generated using the methods described herein are capable of producing higher yields of protein product than cells that are selected using only a selection method for the stable expression, e.g., integration of exogenous nucleic acid encoding the recombinant polypeptide. In an embodiment, the cells selected, identified, or generated using the methods described herein produce 2-fold, 3-fold, 4-fold, 5-fold, 6-fold, 7-fold, 8-fold, 9-fold, or 10-fold or more of the product, e.g., recombinant polypeptide, as compared to cells that were not contacted with an inhibitor of protein degradation, or cells that were only selected for stable expression, e.g., integration, of the exogenous nucleic acid encoding the recombinant polypeptide.

METHODS FOR CELL LINE AND RECOMBINANT POLYPEPTIDE PRODUCTION

The current state of the art in both mammalian and microbial selection systems is to apply selective pressure at the level of the transcription of DNA into RNA. The gene of interest is tightly linked to the selection marker making a high level of expression of the selective marker likely to result in the high expression of the gene of interest. Cells which express the selection marker at high levels are able to survive and proliferate, those which do not are less likely to survive and proliferate, e.g., apoptose and/or die. In this way a population of cells can be enriched for cells expressing the selection marker and by implication the gene of interest at high levels. This method has proved very successful for expressing straightforward proteins.

In one aspect, the disclosure provides methods for generating a cell or cell line for producing a product, e.g., a recombinant polypeptide. In another aspect, the disclosure provides methods for producing a product, e.g., a recombinant polypeptide described herein using a cell that is identified, classified, selected, or generated using the methods described herein. Any of the foregoing methods include evaluating, identifying, classifying, or selecting a cell as described herein, e.g., by contacting the cell with an inhibitor of protein degradation, to identify or make a cell that has the capacity for high production of a product, e.g., a recombinant polypeptide. The methods described herein increase the production, e.g., expression and/or secretion of a recombinant polypeptide.

Without wishing to be bound by theory, it is believed that cells capable of higher productivity are less susceptible to inhibitors of protein degradation, and therefore, it is believed that contacting the cells with an inhibitor of protein degradation comprising an exogenous nucleic acid described herein results in the selection for a cell capable of higher productivity.

In some embodiments, additional steps may be performed to improve the expression of the product, e.g., transcription, translation, and/or secretion of the product, or the quality of the product, e.g., proper folding and/or fidelity of the primary sequence. Such additional steps include introducing an agent that improves product expression or product quality. In an embodiment, an agent that improves product expression or product quality can be a small molecule, a polypeptide, or a nucleic acid that encodes a polypeptide that improves protein folding, e.g., a chaperone protein. In one embodiment, the nucleic acid comprises an inhibitory nucleic acid, e.g., a microRNA or a lncRNA. In an embodiment, the agent that assists in protein folding comprises a nucleic acid that encodes a chaperone protein, e.g., BiP, PD1, or ERO1 (Chakravarthi & Bulleid 2004; Borth et al. 2005; Davis et al. 2000). Other additional steps to improve yield and quality of the product include overexpression of transcription factors such as SBP1 and ATF6 (Tigges & Fussenegger 2006; Cain et al. 2013; Ku et al. 2008) and of lectin binding chaperone proteins such as calnexin and calreticulin (Chung et al. 2004). Overexpression of the agents that assist or improve protein folding and product quality and yield proteins described herein can be achieved by introduction of exogenous nucleic acids encoding the proteins. In another embodiment, the agent that improves product expression or product quality is a small molecule that can be added to the cell culture to increase expression of the product or quality of the product. In one embodiment, culture of the cells at a lower temperature, e.g., 1° C., 2° C., 3° C., 4° C., 5° C., 6° C., 7° C., 8° C., 9° C., or 10° C. lower, than the temperature that the cells are normally grown in.

Any of the methods described herein can further include additional selection steps for identifying cells that have high productivity or produce high quality products. For example, FACS selection can be utilized to select and isolate specific cells with desired characteristics, e.g., higher expression of protein folding proteins, e.g., chaperones; or improved expression of the product.

In one aspect, the disclosure provides methods that include a step for recovering or retrieving the recombinant polypeptide product. In embodiments where the recombinant polypeptide is secreted from the cell, the methods can include a step for retrieving, collecting, or separating the recombinant polypeptide from the cell, cell population, or the culture medium in which the cells were cultured in. In embodiments where the recombinant polypeptide is within the cell, the purification of the recombinant polypeptide product comprises separation of the recombinant polypeptide produced by the cell from one or more of any of the following: host cell proteins, host cell nucleic acids, host cell lipids, and/or other debris from the host cell.

In embodiments, the process described herein provides a substantially pure protein product. As used herein, "substantially pure" is meant substantially free of pyrogenic materials, substantially free of nucleic acids, and/or substantially free of endogenous cellular proteins enzymes and components from the host cell, such as polymerases, ribosomal proteins, and chaperone proteins. A substantially pure protein product contains, for example, less than 25%, 20%, 15%, 10%, 9%, 8%, 7%, 6%, 5%, 4%, 3%, 2%, or 1% of contaminating endogenous protein, nucleic acid, or other macromolecule from the host cell.

Methods for recovering and purification of a product, e.g., a recombinant polypeptide, are well established in the art. For recovering the recombinant polypeptide product, a physical or chemical or physical-chemical method is used. The physical or chemical or physical-chemical method can be a filtering method, a centrifugation method, an ultracentrifugation method, an extraction method, a lyophilization method, a precipitation method, a crystallization method, a chromatography method or a combination of two or more methods thereof. In an embodiment, the chromatography method comprises one or more of size-exclusion chromatography (or gel filtration), ion exchange chromatography, e.g., anion or cation exchange chromatography, affinity chromatography, hydrophobic interaction chromatography, and/or multimodal chromatography.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: Preparation of Anti-GS-CHO Host Cell Protein Polyclonal Antibody

The methods provided in this example are related to the preparation of anti-GS-CHO host cell protein (HCP) polyclonal antibody. The antibody was used for ELISA experiments described in Example 2.
Production of Anti-GS-CHO HCP Antibodies
Three sheep were immunized with HCPs form a GS-CHO null cell line (i.e. CHO-K1SV cells transfected with a blank GS vector). HCPs used as antigen were from cell extract (CE) or cell supernatant (SN). Antigen was prepared according to standard methods (e.g., see The United State pharmacopeia (USP) publishes all the guidelines for the official assay procedure and guidelines. USP<1132> described "Residual host cell protein measurement in biopharmaceuticals" (second supplement to USP 38-NF 33, 7647-7667), published December 2015).
Sheep antisera were collected at various bled dates. The stocked sheep antisera were used to affinity purify anti-GS CHO HCP antibodies.
Purification of anti-GS-CHO HCP Antibodies
The purification process consisted of MabSelect SuRe (MSS) affinity chromatography, concentration/diafiltration, Cyanogen bromide (CNBr) affinity chromatography and a final diafiltration step. Uniquely, the present exemplary process combines Protein A and CNBr chromatography, in a two-step affinity purification. This two-step affinity purification removed the majority of non-specific IgGs (i.e. IgGs which do not bind to HCP). Current purification methods utilize an HCP antibody from the mixture of crude antisera (i.e. without purification) or total IgGs, which has approximately 99% of non-specific IgGs.

Two rounds of purifications were performed, $1^{st}$ and $2^{nd}$ round, with the same conditions. The purification method was tested and confirmed in the Pt round purification with 1800 ml of sheep antisera. The affinity purified anti-GS-CHO HCP antibodies were tested with ELISA, SDS-PAGE, Western blot, and 2D SDS-PAGE for its immunocoverage against GS-CHO HCPs. In the $2^{nd}$ round purification, which started with 8000 ml of antisera, repeated loading with flow through was performed to maximize the production of GS-CHO HCP antibodies in both MSS and CNBr purification.

The IgG titre of raw sheep aintisera was determined by PrA HPLC and the yield of MSS step was 96.33% in the $1^{st}$ round purification and 122.86% in the $2^{nd}$ round purification for CE sheep antisera which were immunized with GS-CHO null cell extracts (the discrepancy of yield over 100% was caused by different method for protein concentration). In total, 10,315 mg of IgGs in the Pt round purification and 60,518 mg of IgGs in the second round purification were eluted from MSS chromatography. The eluted MSS IgGs were to be used for next step of CNBr purification after concentration and diafiltration. In CNBr chromatography, CNBr resin was coupled with GS-CHO cell extracts and used to affinity purify the anti-GS-CHO HCP antibodies from CE MSS IgGs. 39.6 mg of anti-HCP antibodies with a yield of 0.37% were purified in the $1^{st}$ round purification, while 361.2 mg of HCP antibody with a yield of 0.62% were produced in the $2^{nd}$ round purification. Anti-GS-CHO HCP antibodies from the $1^{st}$ round purification were tested for immunocoverage by 2DE Western blot. The coverage against GS-CHO null cell line extract was 72% and 82% against cell extract from a GS-knockout cell line based on spots counting.

The anti-GS-CHO HCP antibodies from the $1^{st}$ and $2^{nd}$ rounds were pooled together to generate a uniform anti-GS-CHO HCP antibody preparation. The total of 391 mg antibody determined by A280 was obtained with an overall cumulative yield of 0.65% for the whole purification process. The final Anti-GS-CHO HCP antibody was tested for immunocoverage by 2DE Western blot. The coverage against GS-CHO null cell line extract was 77% against cell extract from a GS-CHO cell line based on total spots counting, and 71% based on matching spots.

The exemplified purification process described in this example is depicted in FIG. 1. The final anti-GS-CHO HCP antibody was used in the ELISA described in Example 2. The final antibody was also biotinylated for use in the ELISA described in Example 2.

Example 2: GS-CHO HCP ELISA

The methods provided in this example are related a sandwich ELISA developed to detect and quantify GS-CHO HCPs. The ELISA assay conditions were for superior performance to current methods (see e.g., Example 3).

The ELISA was optimized with the affinity purified GS-CHO HCP antibody described in Example 1. The ELISA plate was coated with 100 μl of 2 μg/ml GS-CHO HCP antibody in carbonate/biocarbonate buffer per well, and incubated at 5±3° C. overnight (18±2 hours). The coated plate was washed three times with 300 μl of wash buffer (0.05% Tween® 20 in 1×DPBS), followed by the addition of 300 μl of blocking buffer (0.2% casein in 1×DPBS) per well, and incubated for 60±5 minutes at 23±2° C. with 300±50 rpm shaking. Nine standards (80 ng/ml to 0.31 ng/ml) were prepared by a 1 in 2 serial dilution of GS-CHO HCP standard with blocking buffer. An example dilution scheme is provided in Table 3.

TABLE 3

GS-CHO HCP ELISA Standard Preparation

| Standards | Concentration | Sample (μl) | Blocking Buffer (μl) |
|---|---|---|---|
| N/A | 1 mg/ml | 40 of stock standard | 208 |
| N/A | 10 μg/ml | 10 of 1 mg/ml | 990 |
| Std 1 | 80 ng/ml | 16 of 10 ug/ml | 1984 |
| Std 2 | 40 ng/ml | 1000 of 80 ng/ml | 1000 |
| Std 3 | 20 ng/ml | 1000 of 40 ng/ml | 1000 |
| Std 4 | 10 ng/ml | 1000 of 20 ng/ml | 1000 |
| Std 5 | 5 ng/ml | 1000 of 10 ng/ml | 1000 |
| Std 6 | 2.5 ng/ml | 1000 of 5 ng/ml | 1000 |
| Std 7 | 1.25 ng/ml | 1000 of 2.5 ng/ml | 1000 |
| Std 8 | 0.63 ng/ml | 1000 of 1.25 ng/ml | 1000 |
| Std 9 | 0.31 ng/ml | 1000 of 0.63 ng/ml | 1000 |
| Blank control | 0 ng/ml | N/A | 1000 |

HCP spiking solutions were prepared following the example in Table 4.

TABLE 4

GS-CHO HCP ELISA Spike Solution Preparation

| Spike Solutions | Concentration (ng/ml) | Sample (µl) | Blocking Buffer (µl) |
|---|---|---|---|
| No 1 | 400 | 80 of 10 µg/ml | 1920 |
| No 2 | 200 | 1000 of 400 ng/ml | 1000 |
| No 3 | 100 | 1000 of 200 ng/ml | 1000 |
| No 4 | 40 | 800 of 100 ng/ml | 1200 |
| No 5 | 20 | 1000 of 40 ng/ml | 1000 |

Sample was diluted with blocking buffer at pre-determined dilutions, for example 1 in 5 dilution, 1 in 10 dilution, etc. The plate was washed three times with 300 µl of wash buffer (0.05% Tween® 20 in 1×DPBS). 100 µl prepared samples, and samples were loaded per well in triplicate. The plate was then incubated for 90±5 minutes at 23±2° C. with 300±50 rpm shaking. The plate was washed three times with 300 µl of wash buffer (0.05% Tween® 20 in 1×DPBS), and 100 µl of 2 µg/ml biotinylated SG-CHO HCP antibody diluted in blocking buffer per well. The plate was incubated for 60±5 minutes at 23±2° C. with 300±50 rpm shaking. The plate was washed three times with 300 µl of wash buffer (0.05% Tween® 20 in 1×DPBS), and 100 µl of streptavidin-HRP 1 in 10,000 dilution in blocking buffer was loaded per well. The plate was incubated for 60±5 minutes at 23±2° C. with 300±50 rpm shaking. The plate was washed three times with 300 µl of wash buffer (0.05% Tween® 20 in 1×DPBS), and 100 µl of TMB 1C was loaded per well. The plate was incubated for 10±1 minutes at 23±2° C. with 300±50 rpm shaking. After incubation, the reaction was stopped by adding 50 µl of stop solution (2.5 M sulphuric acid, stored at room temperature) per well. The plate was read by a plate reader at 450 nm wavelength with 630 nm reference. The data were analyzed by SoftMax Pro (Ver 5.4.3) and the standard curve was plotted with 4-parameter logistic fitting.

Example 3: Evaluation of GS-CHO HCP ELISA

The following example provides an evaluation of the GS-CHO HCPs sandwich ELISA described in Example 2. The results of the evaluation are described below.

Accordingly, five GS-CHO bulk purified products, three GS-CHO in-process products and one final formulation buffer were tested to evaluate the GS-CHO HCP ELISA. These test samples were representative of the product samples for the GS-CHO HCP ELISA. The GS-CHO products were diluted using 1 in 2 serial dilutions and tested in the ELISA described in Example 2. Five spike levels, 1, 2, 5, 10, and 20 ng/ml, were tested with the product dilutions. Spike recovery was used to assess the assay performance for each product.

The five bulk purified products (BDS Mab DV, Mab BM, Product A15, Mab DU, and Mab DH) and the three in process samples (Mab CZ, Mab BM, Mab MSS eluates) and Mab BM final formulation buffer were tested. The accuracy, precision, linearity, working range, limit of detection, limit of quantification, and specificity were analyzed and described below.

Accuracy

The accuracy of the ELISA was analyzed by the recovery of all five spike levels. The accuracy of spike levels 5, 10, and 20 ng/ml was within acceptable range of 75% to 125% recovery. For 2 ng/ml, the majority of product dilutions had acceptable recovery within 75% to 125% recovery. High levels of endogenous HCP concentration affected the accuracy of the spike 2 ng/ml. The overall accuracy of spike level at 1 ng/ml was not acceptable due to the effect of high endogenous HCP level.

GS-CHO products, BDS MAb DV, MAb BM, MAb DU and MAb DH, were tested with three dilutions each with the final ELISA method. For the recovery of spike control at 2, 5, 10 and 20 ng/ml, all of the results (n=38) were within 75% to 125%. Five out of 38 recoveries for spike control at 1 ng/ml were out of acceptable recovery. The spike recoveries from five different spike levels were calculated and the accuracy of the method was evaluated based on the spike recovery. The accuracy of the assay was considered acceptable if the overall mean percentage recovery at each HCP spike level was between 75% and 125% recovery. For HCP spike levels of 5, 10 and 20 ng/ml, the overall spike recoveries of all four tested BDS products with three different dilutions each were between 75% and 125% recovery and acceptable. The endogenous HCP tested varied from 1.395 ng/ml to 24.044 ng/ml.

For the HCP spike level of 2 ng/ml, the spike recovery for all four tested BDS product with two different dilutions each, except the low dilution of the BDS products (for example, the 1 in 2 dilution (1 in 2) in BDS MAb DV), were between 75% and 125% recovery and acceptable. The endogenous HCP concentration of BDS product dilution with failed spike recovery varied from 13.467 ng/ml to 24.044 ng/ml. The endogenous HCP concentration of BDS product dilution with acceptable spike recovery ranged from 1.395 ng/ml to 4.536 ng/ml.

For the HCP spike level of 1 ng/ml, the spike recovery for the four tested BDS products with different dilutions were between 75% and 125% recovery and acceptable. Their endogenous HCP concentration ranged from 1.395 ng/ml to 4.536 ng/ml. The recovery for lowest dilutions of BDS products, for example, 1 in 2 dilution (1 in 2) for MAb DV, MAb DU, MAb BM and 1 in 32 dilution (1 in 32) for MAb DH, were out the range of 75% to 125%. The endogenous HCP concentrations of BDS product dilution with failed spike recoveries ranged from 13.467 ng/ml to 24.044 ng/ml.

From the spike recovery and spike levels, it was concluded that the high level endogenous HCP present in the test sample affected the reliability of the measurement of spike recovery at low spike level, for example, 1 ng/ml or 2 ng/ml. Therefore overall the accuracy was considered as acceptable.

Precision

HCP measurement in four GS-CHO BDS (bulk purified) products was analyzed for the repeatability precision and intermediate precision. Both repeatability and intermediate precision were less than 20% CV. The repeatability of HCP concentration in GS-CHO product was at the upper end of acceptable range of 20% CV. The precision was further analyzed with HCP measurement from the inter-assay controls and spike control throughout the evaluation. The repeatability and intermediate precision were less than 15% CV for both the high and low inter-assay controls (IACs). For the spike controls of 1, 2, 5, 10 and 20 ng/ml, the repeatability precision ad intermediate precision were all below 15% CV.

The repeatability (intra-assay) and intermediate (inter-assay) precision for the measurement of HCP concentration in GS-CHO BDS products were each determined from six occasions of measurements of endogenous HCP impurity in BDS products. Endogenous HCP concentration in each BDS product was calculated from unspiked sample in each measurement with correction of assay dilution factor. For each measurement, HCP was measured from three different dilutions for each product. The repeatability % CV and intermediate precision % CV of HCP concentration in each product were calculated. The repeatability precision % CV for all four GS-CHO BDS products ranged from 10.7% to 15.0%. The repeatability precision % CV was acceptable compared to the target of □20%. Note the repeatability was calculated for results across all dilutions. The intermediate precision % CV for all four GS-CHO BDS products ranged from 7.5% to 16.2% (n=18), which was considered as acceptable compared to the target of ≤20%.

Linearity

Linearity is an important assay parameter which demonstrates that the assay response is proportional to the analyte concentration in test sample, thus response from sample can be interpreted directly from the dose-response calibration curve. The linearity of GS-CHO HCP ELISA was assessed with the HCP measurement with five levels of HCP spiked GS-CHO products. The linearity ($r^2$) value ranged from 0.984 to 1.000 in each assay of accuracy study and four tested GS-CHO HCP products.

Working Range

The working range of GS-CHO HCP ELISA standard curve was determined as the range of 2 ng/ml to 80 ng/ml with acceptable accuracy. The working range was also tested and confirmed with HCP measurements for GS-CHO BDS products.

Limit of Detection

The limit of detection (LOD) of GS-CHO HCP ELISA was determined as 0.9 ng/ml, which was the highest LOD calculated from standard curve in all 6 assays occasions with 41 plates for four GS-CO BDS products. The LOD of each assay (plate) was calculated from the HCP concentration interpreted from standard curve with the mean absorbance of blank control (the standard of 0 ng/ml) plus 2.5 times its standard deviation which provided a significantly different signal. The highest LOD from all tested plates was 0.875 ng/ml, which was rounded up to 0.9 ng/ml. 0.9 ng/ml was defined as the LOD of the GS-CHO HCP ELISA.

Limit of Quantification

The limit of detection (LOQ) of GS-CHO HCP ELISA was determined as 2 ng/ml. The limit of quantitation (LOQ) of the GS-CHO HCP ELISA was defined with the combination of acceptable back-calculated standards and the acceptable accuracy for the tested GS-CHO products. The lowest standard of GS-CHO HCP ELISA with acceptable back calculation (% RE≤15%) and repeatability precision (% CV≤20%) was 1.25 ng/ml. The LOQ for each product with acceptable recovery (between 75% to 125% in at least three out of six occasions) is summarized in Table 12. The LOQ for current standard CHO HCP ELISAs is about 200 ng/ml.

TABLE 5

Limit of Quantitation for GS

| GS-CHO Product | Dilution | LOQ (ng/ml) | Determined LOQ (ng/ml) |
|---|---|---|---|
| MAb DV | 1 in 2 | 5 | 2 |
|  | 1 in 16 | 2* |  |
|  | 1 in 32 | 2* |  |
| MAb DU | 1 in 2 | 5 | 2 |
|  | 1 in 16 | 2* |  |
|  | 1 in 32 | 2* |  |
| MAb BM | 1 in 2 | 5 | 2 |
|  | 1 in 8 | 2 |  |
|  | 1 in 16 | 1 |  |

TABLE 5-continued

Limit of Quantitation for GS

| GS-CHO Product | Dilution | LOQ (ng/ml) | Determined LOQ (ng/ml) |
|---|---|---|---|
| MAb DH | 1 in 32 | 5 | 1 |
|  | 1 in 128 | 1 |  |
|  | 1 in 256 | 1 |  |

*The mean recovery of 1 ng/ml was acceptable but the individual result from each of six occasions was variable and thus not acceptable.

Specificity

The specificity of GS-CHO HCP ELISA was tested against the impurities of Protein A and CHO DNA which might be co-purified with CHP during the purification process. The specificity % for both protein A and CHO DNA was within 97% to 103%. The cross reactivity % was less than 1% in both Protein A and CHO DNA. The specificity result suggested that no potential negative or positive bias from Protein A and CHO DNA was observed in GS-CHO HCP ELISA while measuring HCP in antibody products.

In summary, the exemplary results described herein demonstrate a robust, sensitive HCP ELISA platform assay to support multiple expression systems, including e.g., mammalian expression systems, e.g., the CHOK1SV expression system. The polyclonal HCP antibody raised in sheep was affinity purified and the immunocoverage of the antibody against the cell extract from mock transfected null cells was 71% assessed by spots matching of two dimensional (2D) western blot. The antibody concentration, buffer system and detection system were optimised during ELISA development for superior immunocoverage and LOQ.

The final robust and sensitive HCP ELISA was evaluated according to the International Council on Harmonisation of Technical Requirements for Registration of Pharmaceuticals for Human Use (ICH) Q2(R1) guidelines. The assay parameters for the HCP ELISA were assessed against the pre-determined criteria. The accuracy, intra-assay precision, intermediate precision and linearity of theoretic HCP concentration against the measured HCP concentration were acceptable. The working range of this ELISA was determined as from 2 ng/ml to 80 ng/ml. The LOQ, limit of quantitation of the HCP ELISA, was defined as 2 ng/ml with acceptable spike recovery based on multiple bulk purified products. The specificity against Protein A and CHO DNA which are major impurity sources together with HCP were also proved to be acceptable.

The HCP ELISA can serve as a platform assay to monitor the HCP impurity during the bio-purification process and final bulk drug substance. The assay may also serve for validation and batch release of products produced in the GS-CHO expression system. Additionally, the methods described herein can be used in conjunction with regulatory requirements for the production of recombinant proteins; as the ICH Q6B 6.2 guidelines state that a suitably sensitive immunoassay should be used to detect the spectrum of HCPs that may be present in biological products.

Stability

The GS-CHO HCP ELISA reagents, specifically the HCP analyte, was tested for stability across storage temperature, time, and freeze thaw condition. Stability of GS-CHO HCP within MAb samples or of additional GS-CHO HCP spiked into MAb samples was evaluated at various time points after being stored at either 5±3° C. or −65° C. or below. The results indicated HCP instability and possible degradation at both temperatures in the t=0 days to t=1 day storage period, but HCP stability in the t=1 day to t=85 days storage period.

For two of three MAb samples where no additional HCP was spiked into the sample, the changes in HCP were less than or equal to 30% at both storage temperatures and were acceptable. This demonstrated that the endogenous HCP that was present in the MAb sample was stable for up to 85 days storage at 5±3° C. or −65° C. or below. It was concluded that the storage temperature of −65° C. or below for HCP testing was suitable for the testing of bulk purified samples and the samples can be stored for up to 85 days at −65° C. or below.

Robustness

To demonstrate that small variation in the sample preparation procedure will not affect the performance of the method, robustness in assay drift, assay incubation times, assay incubation temperature, and assay reagent age were evaluated.

Robustness in assay drift was examined by applying inter-assay controls (IACs) containing high sample pg/ml or low sample pg/ml to wells of an ELISA plate and then, after a delay of 5 minutes, applying a second set of IACs to the ELISA plate and evaluating differences in IACs. The addition of samples at different times in the HCP ELISA did not affect the accuracy or precision of the results of the assay, all results were within the normal assay variability, and the HCP ELISA was defined as robust for the time (up to 5 minutes) required to add samples to the ELISA plate.

Robustness in assay incubation time was examined by applying two MAb samples and IACs containing high sample pg/ml or low sample pg/ml to wells of three ELISA plates and then varying the incubation times of assay steps the ELISA plates were subjected to. The IAC results and the MAb sample results for the three plates were acceptable. All results were within the normal assay variability and the test method was defined as robust to variations in assay incubation time.

Robustness in assay incubation temperature was examined by applying two MAb samples and IACs containing high sample pg/ml or low sample pg/ml to wells of three ELISA plates and then testing one plate at 17° C., one plate at 23° C., and one plate at 27° C. The IAC results and MAb results were acceptable. The intermediate precision for the spike control and HCP spike in the MAb sample was acceptable for all three plates. Overall, all results were within the normal assay variability and the test method was defined as robust to variations in assay incubation temperature of 17±2° C. to 25±2° C.

Robustness in assay reagent age was examined by using assay reagents (coating buffer, blocking buffer, and wash buffer) prepared 1 week, two weeks, three weeks, and four weeks after initial preparation. Overall, it was concluded that the assay reagents are stable for up to one month.

What is claimed is:

1. A method of producing a polyclonal anti-host cell protein (HCP) antibody preparation, the method comprising:
    a) acquiring a sample comprising antibodies from an animal immunized with HCP of a host cell;
    b) separating antibodies from the sample by contacting the sample with a protein A affinity reagent to provide an antibody preparation; and
    c) separating anti-HCP antibody from the antibody preparation by contacting the antibody preparation with an HCP-affinity reagent comprising HCP coupled to a substrate;
    thereby producing a polyclonal anti-HCP antibody preparation,
    where in the method excludes an acid inactivation step.

2. The method of claim 1, wherein the substrate coupled to HCP is an N-hydroxysuccinimide (NHS)-derivatized substrate.

3. The method of claim 1, wherein the substrate coupled to HCP is a cyanogen bromide (CNBr)-derivatized substrate.

4. The method of claim 1, wherein the host cell is a mammalian cell.

5. The method of claim 4, wherein the mammalian cell is a CHO cell.

6. The method of claim 1, wherein the method removes at least 50% non-HCP specific IgGs.

7. The method of claim 1, wherein the polyclonal anti-HCP antibody preparation produced contains no more than 50% non-HCP specific IgGs.

8. The method of claim 1 wherein the animal immunized with HCP of a host cell is a sheep or goat.

* * * * *